(12) United States Patent
Bar-Or et al.

(10) Patent No.: US 8,329,012 B2
(45) Date of Patent: Dec. 11, 2012

(54) METHOD AND APPARATUS FOR MEASURING OXIDATION-REDUCTION POTENTIAL

(75) Inventors: Raphael Bar-Or, Denver, CO (US); David Bar-Or, Englewood, CO (US); Leonard T. Rael, Centennial, CO (US)

(73) Assignee: Institute for Molecular Medicine, Inc., Greenwood Village, CO (US)

( * ) Notice: Subject to any disclaimer, the term of this patent is extended or adjusted under 35 U.S.C. 154(b) by 0 days.

(21) Appl. No.: 13/450,743

(22) Filed: Apr. 19, 2012

(65) Prior Publication Data
US 2012/0217159 A1 Aug. 30, 2012

Related U.S. Application Data

(63) Continuation of application No. 13/407,517, filed on Feb. 28, 2012.

(60) Provisional application No. 61/447,568, filed on Feb. 28, 2011.

(51) Int. Cl.
*G01N 27/403* (2006.01)
(52) U.S. Cl. .............. 204/435; 204/400; 204/403.01
(58) Field of Classification Search .......... 204/400, 204/416–418, 435, 403.01; 205/775, 782, 205/785.5, 789
See application file for complete search history.

(56) References Cited

U.S. PATENT DOCUMENTS

| | | | |
|---|---|---|---|
| 3,956,094 A | 5/1976 | Capuano | |
| 4,053,381 A | 10/1977 | Hamblen et al. | |
| 4,225,410 A | 9/1980 | Pace | |
| 4,299,919 A | 11/1981 | Jellinek | |
| 4,545,382 A | 10/1985 | Higgins et al. | |
| 4,571,292 A | 2/1986 | Liu et al. | |
| 4,865,717 A | 9/1989 | Setter et al. | |
| 4,963,245 A | 10/1990 | Weetall | |
| 5,073,011 A | 12/1991 | Ito et al. | |
| 5,165,406 A | 11/1992 | Wong | |
| 5,228,972 A | 7/1993 | Osaka et al. | |
| 5,230,786 A * | 7/1993 | Preidel ..................... 204/435 |

(Continued)

FOREIGN PATENT DOCUMENTS

DE 202005009988 10/2005

(Continued)

OTHER PUBLICATIONS

Derwent English language abstract of Miyawakai JP 60-62978 A, patent published Apr. 11, 1985.*

(Continued)

*Primary Examiner* — Alex Noguerola
(74) *Attorney, Agent, or Firm* — Sheridan Ross P.C.

(57) ABSTRACT

Methods and systems for measuring the oxidation-reduction potential of a fluid sample are provided. The system includes a test strip with a sample chamber adapted to receive a fluid sample. The sample chamber can be associated with a filter membrane. The test strip also includes a reference cell. The oxidation-reduction potential of a fluid sample placed in the sample chamber can be read by a readout device interconnected to a test lead that is in electrical contact with the sample chamber, and a reference lead that is in electrical contact with the reference cell. Electrical contact between a fluid sample placed in the sample chamber and the reference cell can be established by a bridge. The oxidation-reduction potential may be read as an electrical potential between the test lead and the reference lead of the test strip.

18 Claims, 16 Drawing Sheets

U.S. PATENT DOCUMENTS

| | | | |
|---|---|---|---|
| 5,260,321 A | 11/1993 | Hof et al. | |
| 5,267,569 A | 12/1993 | Lienhard | |
| 5,273,639 A | 12/1993 | Kaneko et al. | |
| 5,290,519 A | 3/1994 | Bar-Or et al. | |
| 5,312,590 A | 5/1994 | Gunasingham | |
| 5,334,305 A | 8/1994 | Okada et al. | |
| 5,384,031 A * | 1/1995 | Anderson et al. | 204/435 |
| 5,393,391 A | 2/1995 | Dietze et al. | |
| 5,395,755 A | 3/1995 | Thorpe et al. | |
| 5,401,376 A | 3/1995 | Foos et al. | |
| 5,509,410 A * | 4/1996 | Hill et al. | 600/393 |
| 5,562,815 A | 10/1996 | Preidel | |
| 5,582,698 A | 12/1996 | Flaherty et al. | |
| 5,645,709 A | 7/1997 | Birch et al. | |
| 5,672,811 A | 9/1997 | Kato et al. | |
| 5,679,532 A | 10/1997 | Repine | |
| 5,728,281 A | 3/1998 | Holmstrom et al. | |
| 5,782,879 A | 7/1998 | Rosborough et al. | |
| 5,799,350 A | 9/1998 | Ferek-Petric et al. | |
| 5,820,551 A | 10/1998 | Hill et al. | |
| 5,906,921 A | 5/1999 | Ikeda et al. | |
| 6,143,164 A | 11/2000 | Heller et al. | |
| 6,177,260 B1 | 1/2001 | Benzie et al. | |
| 6,212,417 B1 | 4/2001 | Ikeda et al. | |
| 6,236,873 B1 | 5/2001 | Holmstrom | |
| 6,269,261 B1 | 7/2001 | Ootomo | |
| 6,280,588 B1 | 8/2001 | Kato et al. | |
| 6,294,062 B1 | 9/2001 | Buck, Jr. et al. | |
| 6,321,101 B1 | 11/2001 | Holmstrom | |
| 6,340,428 B1 | 1/2002 | Ikeda et al. | |
| 6,429,021 B1 | 8/2002 | Qian et al. | |
| 6,447,670 B1 | 9/2002 | Holmstrom | |
| 6,599,746 B1 | 7/2003 | Gumbrecht | |
| 6,607,658 B1 | 8/2003 | Heller et al. | |
| 6,749,740 B2 | 6/2004 | Liamos et al. | |
| 6,790,327 B2 | 9/2004 | Ikeda et al. | |
| 6,793,632 B2 | 9/2004 | Sohrab | |
| 7,063,782 B2 | 6/2006 | Wayment et al. | |
| 7,125,723 B2 | 10/2006 | Popov et al. | |
| 7,132,296 B2 | 11/2006 | Ou et al. | |
| 7,134,602 B2 | 11/2006 | Harima | |
| 7,459,066 B2 | 12/2008 | Broadley et al. | |
| 7,618,522 B2 | 11/2009 | Davies | |
| 7,949,473 B2 | 5/2011 | Rauh | |
| 2002/0115619 A1 | 8/2002 | Rubenstein et al. | |
| 2005/0142613 A1 | 6/2005 | Bar-Or et al. | |
| 2005/0244983 A1 | 11/2005 | Ching | |
| 2007/0020181 A1 | 1/2007 | Workman et al. | |
| 2009/0004686 A1 | 1/2009 | Bar-Or et al. | |
| 2010/0267074 A1 | 10/2010 | Bar-Or et al. | |

FOREIGN PATENT DOCUMENTS

| | | | |
|---|---|---|---|
| JP | 60-62978 A * | 4/1985 | |
| JP | 2010-96724 A * | 4/2010 | |
| RU | 2241997 | 12/2004 | |
| WO | WO 03/071266 | 8/2003 | |
| WO | WO 2004/068140 | 8/2004 | |
| WO | WO 2007/039775 | 4/2007 | |
| WO | WO 2007/059455 | 5/2007 | |

OTHER PUBLICATIONS

JPO computer-generated English language translation of the Claim and Detailed Description sections of Suzuki et al. JP 2010-96724 A, patent published Apr. 30, 2010.*

Alonso De Vega et al., "Oxidative Stress in Critically Ill Patients with Systemic Inflammatory Response Syndrome," Critical Care Medicine, vol. 30, No. 8 (Aug. 2002), pp. 1782-1786, (Abstract).

Alonso De Vega et al., "Plasma Redox Status Relates to Severity in Critically Ill Patients," Critical Care Medicine, vol. 28, No. 6 (Jun. 2000), pp. 1812-1814, (Abstract).

Ascensão et al., "Biochemical Impact of a Soccer Match—Analysis of Oxidative Stress and Muscle Damage Markers Throughout Recovery," Clinical Biochemistry, vol. 41, No. 10-11 (Jul. 2008), pp. 841-851, (Abstract).

Author Unknown, "Glucose meter," available at http://en.wikipedia.org/wiki/Glucose_meter, printed on Jun. 14, 2009, 7 pages.

Author Unknown, "Materials for Diagnostic Assays," PALL Life Sciences, Mar. 2009, 8 pages.

Author Unknown, "Orion pH, ORP and ISE Theory," Thermo Electron Corporation, Mar. 24, 2004, 9 pages.

Author Unknown, "Oxidation Reduction Potential (ORP): A New Tool for Evaluating Water Sanitation", Hybrid, Hendrix Genetics Company, Dec. 17, 2010, 4 pages.

Author Unknown, "Redox electrode," Unisense Science, as late as Jun. 6, 2009, 2 pages.

Author Unknown, "Universal Reduction-Oxidation (REDOX) electrode for the Temporal Measurement of the Redox Potential Health and Disease," VCU Technology Transfer Marketing Flyer, as early as Apr. 12, 2007, 2 pages, available at http://www.research.vcu.edu/ott/licensable_technologies/flash/05-70_ward.htm.

Baig et al., "Comparison between Bed Side Testing of Blood Glucose by Glucometer vs Centralized Testing in a Tertiary Care Hospital," J. Ayub Med Coli Abbottabad vol. 19(3), 2007, 5 pages.

Bar-Or et al., "Heterogeneity and Oxidation Status of Commerical Human Albumin Preparations in Clinical Use," Critical Care Medicine, Jul. 2005, vol. 33, No. 7, pp. 1638-1641.

Bayir et al., "Assessment of Antioxidant Reserves and Oxidative Stress in Cerbrospinal Fluid after Severe Traumatic Brain Injury in Infants and Children," Pediatric Research, 2002, vol. 51(5), pp. 571-578.

Biffl et al., "Plasma from Aged Stored Red Blood Cells Delays Neutrophil Apoptosis and Primes for Cytotoxicity: Abrogation by Poststorage Washing but not Prestorage Leukoreduction," The Journal of Trauma, vol. 50, No. 3 (Mar. 2001), pp. 426-432, (Abstract).

Brittingham et al., "Febrile Transfusion Reactions Caused by Sensitivity to Donor Leukocytes and Platelets," Journal of the American Medical Association, vol. 165, No. 7 (Oct. 19, 1957), pp. 819-825, (Abstract).

Carballal et al., "Sulfenic Acid Formation in Human Serum Albumin by Hydrogen Peroxide and Peroxynitrite," Biochemistry, vol. 42 (2003), pp. 9906-9914.

Cases et al., "Response of antioxidant defences to oxidative stress induced by prolonged exercise: antioxidant enzyme gene expression in lymphocytes," European Journal of Applied Physiology, vol. 98, No. 3 (Oct. 2006), pp. 263-269.

Codd et al., "Redox Maintenance and Organ Preservation," Transplantation Proceedings, vol. 9, No. 3 (Sep. 1977), pp. 1569-1571, (Abstract).

Codd et al., "Redox Maintenance in Restoration of Organ Viability," The Journal of Surgical Research, vol. 22, No. 5 (May 1977), pp. 585-592, (Abstract).

Collins et al., "Optimal Redox Electrode Potential for 24-Hour Rabbit Kidney Perfusion," The Journal of Surgical Research, vol. 39, No. 3 (Sep. 1985), pp. 246-250, (Abstract).

Cowley et al., Plasma antioxidant potential in sever sepsis: A comparison of survivors and nonsurvivors, Critical Care Medicine, vol. 24, No. 7 (Jul. 1996), pp. 1179-1183, available at http://www.ccmjournal.com/pt/re/ccm/fulltext.ooo03246-199607000-00019htm;jsessionid=F2GT . . . .

Dosek et al., "High Altitude and Oxidative Stress," Respiratory Physiology & Neurobiology, vol. 158, No. 2-3 (Sep. 30, 2007), pp. 128-131, (Abstract).

EcoScan 5 & 6 Series, Economy Handheld, Eutech Instruments, May 16, 2007, 12 pages.

Elokda et al., "Effects of Exercise Training on the Gluthathione Antioxidant System," European journal of Cardiovascular Prevention and Rehabilitation : Official Journal of the European Society of Cardiology, Working Groups on Epidemiology & Prevention and Cardiac Rehabilitation and Exercise Physiology, vol. 14, No. 5 (Oct. 2007), pp. 630-637, (Abstract).

Ferretti et al., "Copper-induced Oxidative Damage on Astrocytes: Protective Effect Exerted by Human High Density Lipoproteins," Biochimica et biophysica acta, vol. 1635, No. 1 (Nov. 30, 2003), pp. 48-54. (Abstract).

Ferretti et al., "Paraoxonase Activity in High-Density Lipoproteins: A Comparison between Health and Obese Females," The Journal of Clinical Endocrinology & Metabolism, vol. 90, No. 3 (Mar. 2005), pp. 1728-1733.

Ferretti et al., "Protective Effect of Paroxonase Activity in High-density Lipoproteins Against Erythrocyte Membranes Peroxidation: A Comparison Between Healthy Subjects and Type 1 Diabetic Patients," The Journal of Clinical Endocrinology and Metabolism, vol. 89, No. 6 (Jun. 2004), pp. 2957-2962.

Galley et al., "Xanthine Oxidase Activity and Free Radical Generaton in Patients with Sepsis," Critical Care Medicine, vol. 24, No. 10 (Oct. 1996), pp. 1649-1653, (Abstract).

Ghiselli et al., "Total Antioxidant Capacity as a Tool to Assess Redox Status: Critical View and Experimental Data," Free Radical Biology & Medicine, vol. 29, No. 11 (Dec. 2000), pp. 1106-1114, (Abstract).

Gomez-Cabrera et al., "Moderate Exercise in an Antioxidant: Upregulation of Antioxidant genes by Training," Free Radical Biology & Medicine, vol. 44, No. 2 (Jan. 15, 2008), pp. 126-131, (Abstract).

Goode et al., "Decreased Antioxidant Status and Increased Lipid Perosidation in Patients with Septic Shock and Secondary Organ Dysfunction," Critical Care Medicine, vol. 23, No. 4 (Apr. 1995), pp. 646-651, (Abstract).

Green et al., "Effluent Redox Potential: A Rapid Method for Assaying Warm Ischemic Injury," The Journal of Surgical Research, vol. 25, No. 3 (Sep. 1978), pp. 222-225, (Abstract).

Horton, "Free Radicals and Lipid Peroxidation Mediated Injury in burn Trauma: The Role of Antioxidant Therapy," Toxicology, vol. 189, No. 1-2 (Jul. 15, 2003), pp. 75-88, (Abstract).

Huang et al., "The Chemistry behind Antioxidant Capacity Assays," Journal of Agriculture and Food Chemistry, vol. 53 (2005), pp. 1841-1856.

Jellinek et al., "Electrochemical Control of Redox Potential in Perfusate for Prolonged Heart Storage," Transactions—American Society for Artificial Internal Organs, vol. 20 (1974), pp. B:533-537, (Abstract).

Jellinek et al., "Oxidation-Reduction Maintenance in Organ Preservation," Archives of Surgery, vol. 120, No. 4 (Apr. 1985), pp. 439-442, (Abstract).

Ji, "Antioxidants and Oxidative Stress in Exercise," Proceedings of the Society for Experimental Biology and Medicine, Society for Experimental Biology and Medicine (New York, N.Y.), vol. 222, No. 3 (Dec. 1999), pp. 283-292.

Ji, "Modulation of Skeletal Muscle Antioxidant Defense by Exercise: Role of Redox Signaling," Free Radical Biology & Medicine, vol. 44, No. 2 (Jan. 15, 2008), pp. 142-152 (Abstract).

Kohen et al., "Noninvasive in vivo evaluation of skin antioxidant activity and oxidation status," Methods in Enzymology, vol. 300 (1999), pp. 428-437.

Kohen et al., "Quantification of the overall reactive oxygen species scavenging capacity of biological fluids and tissues," Free Radical Biology & Medicine, vol. 28, No. 6 (Mar. 15, 2000), pp. 871-879.

Kyparos et al., "Short Duration Exhaustive Aerobic Exercise Induces Oxidative Stress: A Novel Play-oriented Volitional Fatigue Test," The Journal of Sports Medicine and Physical Fitness, vol. 47, No. 4 (Dec. 2007), pp. 483-490, (Abstract).

Lamprecht et al., "Single Bouts of Exercise Affect Albumin Redox State and Carbonyl Groups on Plasma Protein of Trained Men in a Workload Dependent Manner," Journal of Applied Physiology, vol. 104, No. 6 (Jun. 2008), pp. 1611-1617, (Abstract).

Lee et al., "A cobalt-coated needle-type microelectrode array sensor for in situ monitoring of phosphate," J. Micromech. Microeng., vol. 19, 2009, 2 pages, Abstract.

Lee et al., "Fabrication of microelectrode arrays for in situ sensing of oxidation reduction potentials," Sensors & Actuators B: Chem., vol. 115(1), May 23, 2006, 3 pages, Abstract.

Lekhi et al., "Influence of Exercise on Oxidant Stree Products in Elite Indian Cyclists," British Journal of Sports Medicine, vol. 41, No. 10 (Oct. 2007), pp. 691-693, (Abstract).

Lemineur et al., "Biomarkers of oxidative stress in critically ill patients: What should be measured, when and how?" Curr. Opin. Clin. Nutr. Metabol. Care, Nov. 2006, vol. 9(6), pp. 704-710.

Margonis et al., "Oxidative Stress Biomarkers Responses to Physical Overtraining: Implications for Diagnosis," Free Radical Biology and Medicine, vol. 43, No. 6 (Sep. 15, 2007), pp. 901-910, (Abstract).

Mayer et al., "Reduced serum total reductive capacity in lethal severe trauma," The Journal of Trauma, vol. 51, No. 1 (Jul. 2001), pp. 88-91.

McAnulty et al., "Influence of Carbohydrate, Intense Exercise , and Rest Intervals on Homonal and Oxidative Changes," International Journal of Sport Nutrition and Exercise Metabolism, vol. 17, No. 5 (Oct. 2007), pp. 478-490, (Abstract).

Meijer, "Exercise-induced oxidative stress in older adults as measure by antipyrine oxidation," Metabolism, vol. 50, No. 12 (Dec. 2001), pp. 1484-1488, (Abstract).

Michailidis et al., "Sampling Time is Critical for Measurement of Aerobic exercise-induced oxidative Stress," Medicine and Science in Sports and Exercise, vol. 39, No. 7 (Jul. 2007), pp. 1107-1113, (Abstract).

Miller et al., "Acute Respiratory Distress Syndrome in Blunt Trauma: Identification of Independent Risk Factors," The American Surgeon, vol. 68, No. 10 (Oct. 2002), pp. 845-851, (Abstract).

Miller et al., "Improved Myocardial Preservation by Control of the Oxidation-Reduction Potential," The Journal of Heart Transplantation, vol. 4, No. 3 (May 1985), pp. 319-324, (Abstract).

Nikolaidis et al., "Decreased Blood Oxidative Stress After Repeated Muscle-Damaging Exercise," Medicine and Science in Sports and Exercise, vol. 39, No. 7 (Jul. 2007), pp. 1080-1089, (Abstract).

Paschalis et al., "Uniform and Prolonged Changes in Blood Oxidative Stress After Muscle-damaging Exercise," In vivo (Athens, Greece), vol. 21, No. 5 (Sep.-Oct. 2007), pp. 877-883, (Abstract).

Popov et al., "Photochemiluminescent detection of antiradical activity. VI. Antioxidant characeristics of human blook plasma, low density lipoprotein, serum albumin and amino acids during in vitro oxidation," Luminescence, vol. 14, 1999, pp. 169-174.

Popov et al., "Photochemiluminescent detection of antiradical activity. VII. Comparison with a modified method of thermo-initiated free radical generation with chemiluminescent detection," Luminescence, vol. 20, 2005, pp. 321-325.

Prior et al., "In Vivo Total Antioxident Capacity: Comparison of Different Analytical Methods," Free Radical Biology & Medicine, vol. 27, Nos. 11-12 (1999), pp. 1173-1181.

Prokhorov et al., "A method of redoxometry in clinical studies," Vopr. Med. Khim., vol. 35, No. 5 (Sep.-Oct. 1989), pp. 2-6, (Abstract).

Radak et al., "Effects of Exercise on Brain Function: Role of Free Radicals," Applied Physiology, Nutrition, and Metabolism, vol. 32, No. 5 (Oct. 2007), pp. 942-946, (Abstract).

Radak et al., "Exercise, Oxidative Stress and Hormesis," Ageing Research Reviews, vol. 7, No. 1 (Jan. 2008), pp. 34-42, (Abstract).

Radak et al., "Systemic Adaptation to Oxidative Challenge Induced by Regular Exercise," Free radical Biology & Medicine, vol. 44, No. 2 (Jan. 15, 2008), pp. 153-159, (Abstract).

Rael et al., "Combined cupric- and cuprous-binding peptides are effective in preventing IL-8 release from endothelial cells and redox reactions," Biochemical and Biophysical Research Communications, vol. 357 (2007), pp. 543-548.

Rael et al., "Oxidation-reduction potential and paraxonase-arylesterase activity in trauma patients," Biochemical and Biophysical Research Communications, vol. 361 (2007), pp. 561-565.

Rael et al., "Plasma oxidation-reduction potential and protein oxidation in traumatic brain injury," J. Neurotrauma, Aug. 2009, vol. 26(8), pp. 1203-1211.

Rael et al., "The effect of storage on the accumulation of oxidative biomarkers in donated packed red blood cells," J. Trauma, Jan. 2009, vol. 66(1), pp. 76-81.

Rahnama et al., "Oxidative Stress responses in Physical Education Students During 8 Weeks Aerobic Training," The Journal of Sports Medicine and Physical Fitness, vol. 47, No. 1 (Mar. 2007), pp. 119-123, (Abstract).

Rana et al., "Study on Oxidative Stress in Patients with Abdominal Trauma," Molecular and Cellular Biochemistry, vol. 291, No. 1-2 (Oct. 2006), pp. 161-166, (Abstract).

Rao et al., "Redox Potential Measurements of Plasma in Patients Undergoing Coronary Artery Bypass Graft and Its Clinical Significance," Journal of Pharmacological and Toxicological Methods, vol. 38 (1997), pp. 151-156.

Rice-Evans, "Measurement of Total Antioxidant Activity as a Marker of Antioxidant Status in Vivo: Procedures and Limitations," Free Radical Research, vol. 33, Supplement (Nov. 2000), pp. 59-66, (Abstract).

Roth et al., "Assessing the antioxidative status in critically ill patients," Current Opinion in Clinical Nutrition and Metabolic Care, vol. 7 (2004), pp. 161-169.

Sauaia et al., "Early Predictors of Postinjury Multiple Organ Failure," Archives of Surgery, vol. 129, No. 1 (Jan. 1994), pp. 39-45, (Abstract).

Sen et al., "Antioxidants in Exercise Nutrition," Sports Medicine (Auckland, N.Z.), vol. 31, No. 13 (2001), pp. 891-898, (Abstract).

Shin et al., "Exercise Training Improves the Antioxidant Enzyme Activity with no Change of Telomere Length," Mechanisms of Ageing and Development, vol. 129, No. 5 (May 2008), pp. 254-260, (Abstract).

Shing et al., "The Effect of Consecutive Days of Exercise on Markers of Oxidative Stress," Applied Physiology, Nutrition, and Metabolism, vol. 32, No. 4 (Aug. 2007), pp. 677-685, (Abstract).

Soffler, "Oxidative Stress," The Veterinary Clinics of North America. Equine Practice, vol. 23, No. 1 (May 2007), pp. 135-157 (Abstract).

Steinberg et al., "Cytokine and Oxidative responses to Maximal Cycling Exercise in Sedentary Subjects," Medicine and Science in Sports and Exercise, vol. 39, No. 6 (Jun. 2007), pp. 964-968, (Abstract).

Veglia et al., "Age- and gender-related oxidative status determined in healthy subjects by means of OXY-SCORE, a potential new comprehensive index," Biomarkers, vol. 11, No. 6 (Nov.-Dec. 2006), pp. 562-573.

Vollard et al., "Exercise-induced oxidative stress: Myths, realities and physiological relevance," Sports Med., 2005, vol. 35(12), pp. 1045-1062.

Williams et al., "Dietary Supplements and Sports Performance: Introduction and Vitamins," Journal of the International Society of Sports Nutrition, vol. 1, No. 2 (2004), pp. 1-6.

Winterbourn et al., "Protein Carbonyl Measurements Show Evidence of Early Oxidative Stress in Critically Ill Pateints," Critical Care Medicine, vol. 28, No. 1 (Jan. 2000), pp. 275-277 (Abstract).

Yu et al., "Stratification and Oxidation-Reduction Potential Change in an Aerobic and Sulfate-Reducing Biofilm Studied Using Microelectrodes," JSTOR: Water Environment Research, vol. 73, No. 3, May-Jun. 2001, 2 pages, Abstract.

Zoppi et al., "Overreaching-induced oxidative stress, enhanced HSP72 expression, antioxidant and oxidative enymes downregulaltion," Scandinavian Journal of Medicine & Science in Sports, vol. 18, No. 1 (Feb. 2008), pp. 67-76 (Abstract).

Written Opinion for International (PCT) Patent Application No. PCT/US08/63855, mailed Aug. 26, 2008.

International Search Report for International (PCT) Patent Application No. PCT/US08/63855, mailed Aug. 26, 2008.

International Preliminary Report on Patentability for International (PCT) Patent Application No. PCT/US08/63855, mailed Nov. 24, 2009.

Extended European Search Report for European Patent Application No. 08755661.9, dated Aug. 3, 2010.

Bar-Or et al. U.S. Appl. No. 13/601,586, filed Aug. 31, 2012.

Cernak et al. "Characterization of Plasma Magnesium Concentration and Oxidative Stress Following Graded Traumatic Brain Injury in Humans," Journal of Neurotrauma, Jan. 2000, vol. 17, No. 1, pp. 53-68.

Rosenberg et al. "Who bounces back? Physiologic and other predictors of intensive care unit readmission," Critical Care Medicine, Mar. 2001, vol. 29, No. 3, pp. 511-518.

International Search Report for International (PCT) Patent Application No. PCT/US2012/026884, mailed Jun. 21, 2012 4 pages.

Written Opinion for International (PCT) Patent Application No. PCT/US2012/026884, mailed Jun. 21, 2012 6 pages.

Official Action for U.S. Appl. No. 13/407,517, mailed Sep. 5, 2012 25 pages.

* cited by examiner

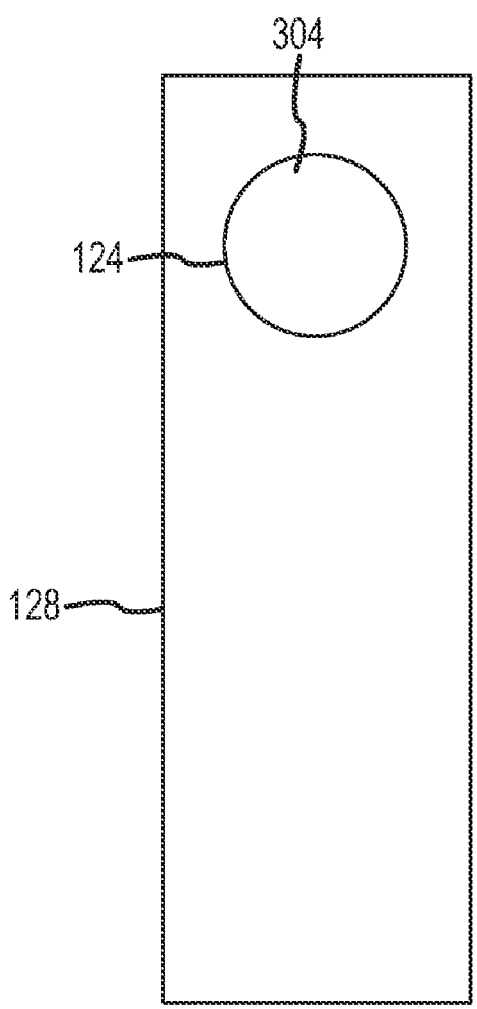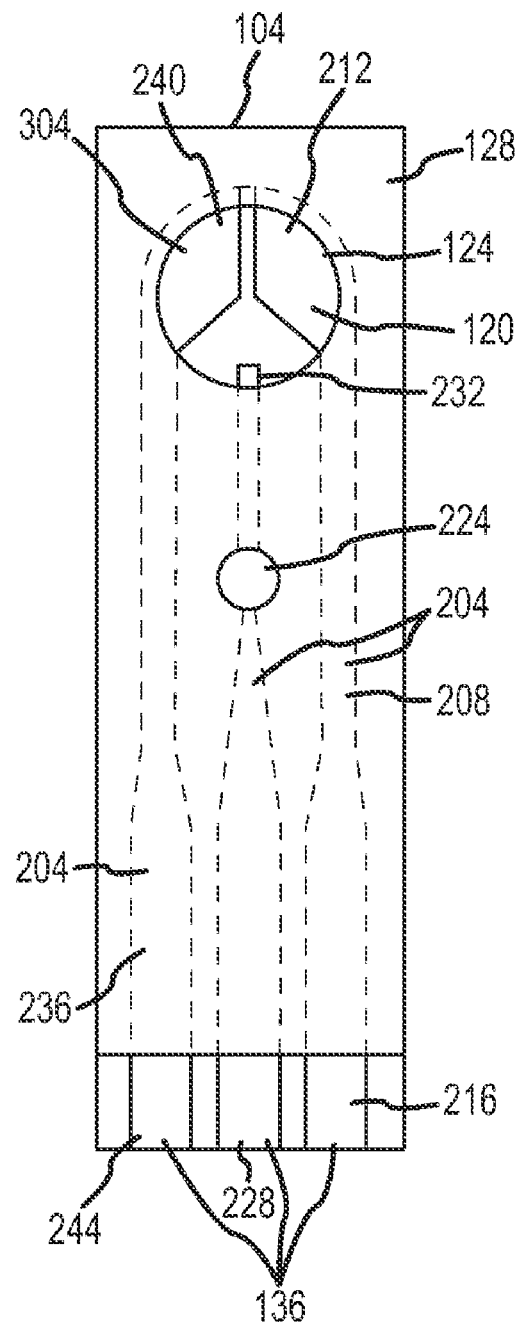
FIG.3
FIG.4

METHOD AND APPARATUS FOR MEASURING OXIDATION-REDUCTION POTENTIAL

CROSS-REFERENCE TO RELATED APPLICATIONS

This application is a continuation of U.S. patent application Ser. No. 13/407,517, filed Feb. 28, 2012, which claims the benefit of U.S. Provisional Patent Application Ser. No. 61/447,568, filed Feb. 28, 2011, the entire disclosures of which are hereby incorporated herein by reference.

FIELD

The present invention relates to methods and apparatuses for measuring the oxidation-reduction potential of a fluid sample.

BACKGROUND

Whole blood and blood products, such as plasma and serum, have oxidation-reduction potentials (ORP). Clinically the ORP of blood, plasma and serum provides a diagnostic assay of the oxidative status of an animal. More particularly, researchers have determined that the ORP of blood, plasma and serum is related to health and disease.

An oxidation-reduction system, or redox system, involves the transfer of electrons from a reductant to an oxidant according to the following equation:

$$\text{oxidant} + ne^- \leftrightarrow \text{reductant} \qquad (1)$$

where $ne^-$ equals the number of electrons transferred. At equilibrium, the redox potential (E), or oxidation-reduction potential (ORP), is calculated according to the Nernst-Peters equation:

$$E(\text{ORP}) = E_o - RT/nF \ln [\text{reductant}]/[\text{oxidant}] \qquad (2)$$

where R (gas constant), T (temperature in degrees Kelvin) and F (Faraday constant) are constants. $E_o$ is the standard potential of a redox system measured with respect to a hydrogen electrode, which is arbitrarily assigned an $E_o$ of 0 volts, and n is the number of electrons transferred. Therefore, ORP is dependent on the total concentrations of reductants and oxidants, and ORP is an integrated measure of the balance between total oxidants and reductants in a particular system. As such, ORP provides a measure of the overall oxidative status of a body fluid or tissue of a patient.

An ORP measurement which is significantly higher than that of normals will indicate the presence of oxidative stress. Oxidative stress has been related to many diseases, and it has been found to occur in all types of critical illnesses. Accordingly, an ORP level significantly higher than that of normals indicates the presence of a disease and perhaps a critical illness. An ORP measurement which is the same as or lower than that of normals indicates the absence of oxidative stress and the absence of a disease or critical illness. Thus, the ORP level of a patient can be used by a medical doctor or veterinarian as an aid in diagnosing or ruling out the presence of a disease, particularly a serious illness. Sequential measurements of ORP over time can be used to monitor the progression of a disease and the effectiveness or lack of effectiveness of treatment of the disease. If a patient's ORP does not decrease after treatment, or especially if it increases despite treatment, this may indicate a poor prognosis and the need for more aggressive and/or additional and/or different treatments. In the case of a measurement made by a patient, such as a patient experiencing symptoms of myocardial infarction, the ORP level may indicate the need for the patient to see a doctor or to immediately proceed to an emergency room for treatment.

Oxidative stress is caused by a higher production of reactive oxygen and reactive nitrogen species or a decrease in endogenous protective antioxidative capacity. Oxidative stress has been related to various diseases and aging, and it has been found to occur in all types of critical illnesses. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. Several investigations have shown a close association between the oxidative status of a critically ill patient and the patient's outcome. See Roth et al., *Current Opinion in Clinical Nutrition and Metabolic Care*, 7:161-168 (2004).

Oxidative stress in patients has been evaluated by measuring various individual markers. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. However, such measurements are often unreliable and provide conflicting and variable measurements of the oxidative status of a patient. See Veglia et al., *Biomarkers*, 11(6): 562-573 (2006); Roth et al., *Current Opinion in Clinical Nutrition and Metabolic Care*, 7:161-168 (2004). The measurement of multiple markers which are then used to provide a score or other assessment of the overall oxidative status of a patient has been developed to overcome the problems of using measurements of single markers. See Veglia et al., *Biomarkers*, 11(6): 562-573 (2006); Roth et al., *Current Opinion in Clinical Nutrition and Metabolic Care*, 7:161-168 (2004). Although such approaches are more reliable and sensitive than measurements of a single marker, they are complex and time consuming. Thus, there is a need for a simpler and faster method for reliably measuring the overall oxidative status of a patient.

The oxidation/reduction potential can be measured electrochemically. Electrochemical devices for measuring ORP of blood and blood products typically require large sample volumes (that is, ten to hundreds of milliliters) and long equilibrium periods. Furthermore, the electrochemical devices have large, bulky electrodes that require cleaning between sample measurements. Such electrochemical devices are poorly suited for routine clinical diagnostic testing. It has been suggested to use electrodes that have undergone treatment to prevent biofouling. However, such devices necessarily involve complex manufacturing techniques. Moreover, conventional electrochemical devices have not provided a format that is convenient for use in a clinical setting.

The oxidative and radical characteristics of human blood plasma and its blood components (such as low density lipoproteins, serum albumin, and amino acids) can also be determined from photo chemiluminescence, with and without thermo-initiated free radical generation. A photo chemiluminescent system generally includes a free radical generator and a detector that measures chemiluminometric changes in the presence of an antioxidant. More specifically, the blood plasma sample (or one of its components) containing an amount of antioxidant is contacted and reacted with a known amount of free radicals. The free radicals remaining after contacting the blood plasma sample are determined chemiluminometrically. This type of measurement and detection system is not suitable for rapid, large scale measurements of blood plasma samples in a clinical setting.

SUMMARY

Embodiments of the present invention are directed to solving these and other problems and disadvantages of the prior art, and provide systems and methods for measuring oxidation-reduction potential (ORP) that are suitable for rapid, routine clinical diagnostic testing. The system generally includes a test strip and a readout device. More particularly, embodiments of the present invention system can determine the ORP of a body fluid of a patient, including blood, plasma and serum, or a fluid from an in vitro source, such as, but not limited to extracellular and intracellular fluids (as for example, aqueous humour, vitreous humour, breast milk, cerebrospinal fluid, cerumen, endolymph, perilymph, gastric juice, mucus, peritoneal fluid, pleural fluid, salvia, sebum, semen, sweat, tears, vaginal secretion, vomit, and urine).

The test strip generally includes a substrate, one or more test leads, a reference lead, a reference cell, and a bridge. In a preferred embodiment, the one or more test leads, the reference lead, the reference cell and the bridge are located between an overlay and the substrate. A sample chamber generally encompasses at least a portion of the bridge and a portion of each of the one or more test leads. The one or more test leads may comprise a working electrode and a counter electrode. In one embodiment, a sample region comprising the sample chamber is defined by an aperture, the aperture being contained within the overlay. Alternatively or in addition, the sample chamber includes a depression or well within the substrate, or an aperture or well in an intermediate layer. The sample chamber is generally configured to contain a fluid sample, such as blood and/or a blood product. The fluid sample generally comprises a volume of less than about 1 ml. Preferably, the volume of the fluid sample is about a drop of blood (e.g., 0.05 ml) or less. In accordance with embodiments of the present invention, the bridge is wetted by the fluid sample, to place the bridge and at least portions of the sample chamber in electrical contact with the reference cell.

The substrate can comprise a dielectric material and may have a substantially planar surface. In accordance with embodiments of the present invention, the overlay may comprise a dielectric material. The overlay may be bonded or laminated to the substrate.

The leads generally comprise an electrically conductive material having a substantially continuous and/or uniform composition. More particularly, the leads may comprise a noble metal or other electrically conductive material. As an example, the leads may comprise an electrically conductive ink that is deposited on the substrate in a printing process. The one or more test leads generally extend from the sample chamber to a readout region, and the reference lead generally extends from the reference cell to the readout region. The readout region contains electrical contacts associated with the leads, and is generally adapted to operatively interconnect to the readout device and to form an electrical contact between the readout device and at least one test lead and the reference lead.

The reference cell generally provides a known voltage potential. Without limitation, the reference cell can comprise one of a silver/silver chloride half-cell, a copper/copper sulfate half-cell, a mercury/mercurous chloride half-cell, and a standard hydrogen half-cell.

The bridge is provided to establish electrical contact between a fluid sample in the sample chamber and the reference cell. The bridge can include an electrolytic solution, an ionic gel, a filter, or any water wicking or water transporting material, such as paper. The bridge is generally positioned between the sample chamber and the reference cell.

In practice, electrical contact is established between the leads when a suitable fluid sample is placed in the sample chamber, and the bridge is operative to place the fluid sample and the reference cell in electrical contact with one another. For example, where the bridge comprises a water transporting material, the bridge is operative to establish electrical contact between the fluid sample and the reference cell when the bridge is sufficiently wetted to establish an electrical contact with the reference cell and the fluid sample. Furthermore, an electrical circuit is established when a fluid sample is placed in the sample chamber 120 and two or more of the leads are operatively interconnected to the readout device.

The readout device generally comprises a voltmeter, galvanostat, potentiostat or other device that is capable of reading a potential difference comprising or representative of the ORP of the fluid sample by electrically interconnecting to the working electrode, the counter electrode, and/or the reference lead of the test strip. Examples of suitable readout devices include, without limitation, analog voltmeters, digital voltmeters, analog null-balance voltmeters, galvanostats, and potentiostats. In some embodiments, the readout device can have a processor that includes and/or is associated with a memory for controlling one or more optional aspects of the readout device. Without limitation, the processor can execute instructions stored in memory, can implement a process according to measured voltage, and/or can implement a process according to a time interval. The readout device can further include one or both of a user input and a user output. Examples of the user output include, without limitation, one or more of a digital output that displays an oxidation/reduction potential value, indicator lamp(s), machine generated speech, and an audible tone sequence. Examples of the user input include, without limitation, buttons, switches, a keypad, a keyboard, and/or a touch screen interface for receiving input from the user. The user input can receive input to control one or more of input to: power on or power off the readout device, perform diagnostics related to the proper operation of the readout device, receive input related to various operational parameters or control other operations or functions.

Another aspect of the present invention is a method of using the system to determine the ORP of a sample. The method generally includes the following steps: a) obtaining a fluid sample; b) placing the fluid sample in the sample chamber of the test strip; c) using a bridge to substantially establish electrical contact between the sample chamber the reference cell; d) interconnecting a test electrode and a reference electrode of the test strip to a readout device; e) determining the ORP after a selected interval. In one configuration, step b) further includes separating a plasma component from a whole blood fluid sample, wherein the plasma is collected in the sample chamber. In another configuration, step d) further includes interconnecting a counter electrode to the readout device, passing a current between the working electrode and the counter electrode, and reading a voltage potential between the reference electrode and the working electrode.

BRIEF DESCRIPTION OF THE DRAWINGS

FIG. 3 depicts a test strip overlay component in accordance with embodiments of the present invention;

FIG. 4 illustrates the relationship of components in an assembled test strip in accordance with embodiments of the present invention;

DETAILED DESCRIPTION

Figure 1:
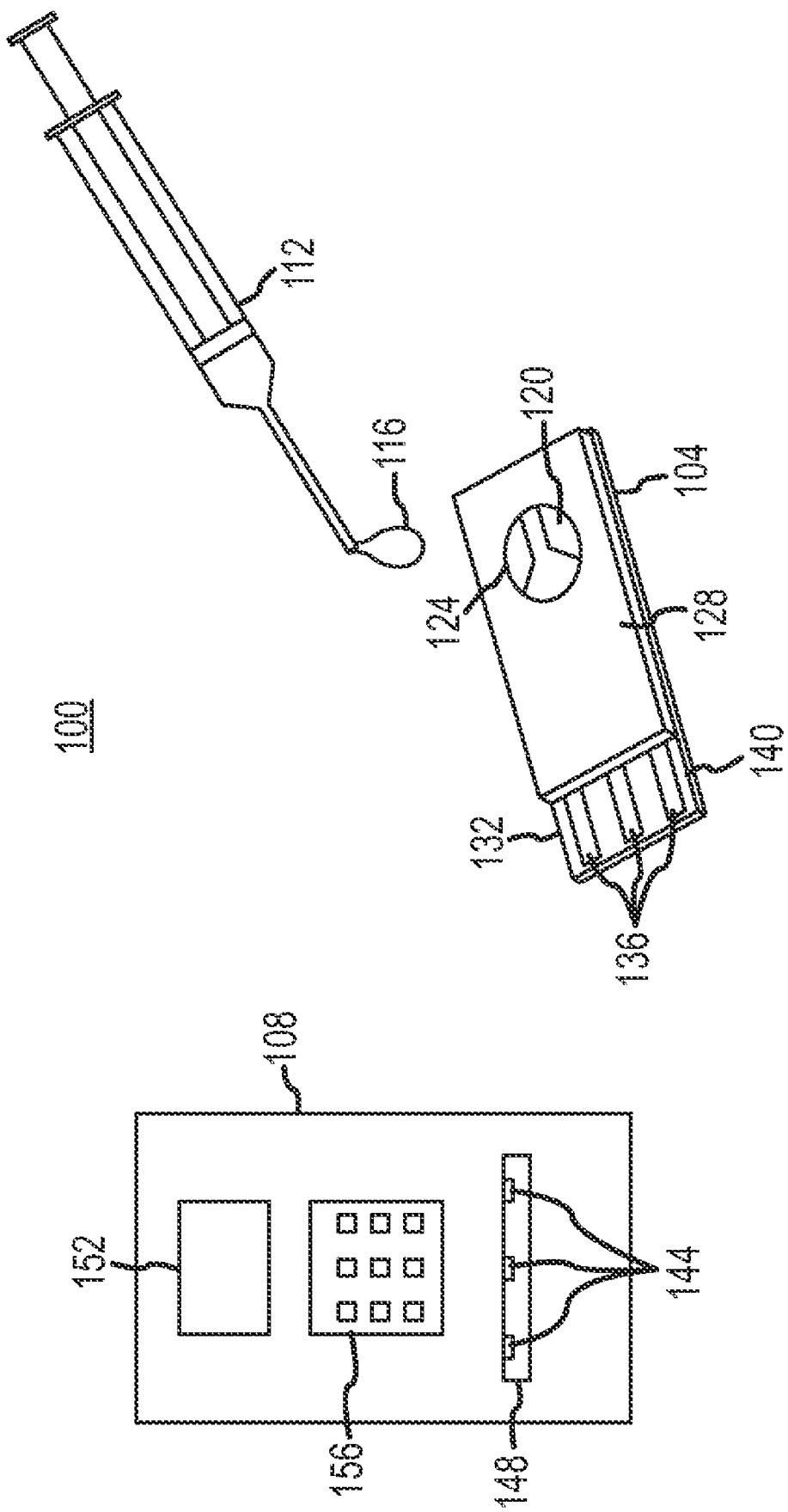
FIG. 1 depicts a system for measuring the oxidation-reduction potential of a fluid in accordance with embodiments of the present invention.

FIG. 1 depicts a system 100 for measuring the oxidation-reduction potential of a fluid sample in accordance with embodiments of the present invention. The system 100 generally includes a test strip 104 and a readout device 108. Also shown as a part of the system 100 is a fluid sample source 112 for supplying a fluid sample 116.

The test strip 104 generally includes a sample chamber 120. The sample chamber 120 may correspond to a test strip overlay aperture 124 formed in a test strip overlay 128. The test strip overlay 128 may be interconnected to a test strip substrate 132. A number of electrical contacts 136 may be provided in a readout region 140. The electrical contacts 136 may be associated with various leads and other components of the test strip 104, as will be described in greater detail elsewhere herein.

The readout device 108 may include a set of readout device contacts 144. The readout device contacts 144 are generally configured to establish an electrical connection between the readout device 108 and the electrical contacts 136 of the test strip 104. As shown in the example system 100, the readout device contacts 144 may be associated with a readout aperture 148 that receives the readout region 140 of the test strip 104 when the test strip 104 is joined with the readout device 108 such that an electrical signal can be read from the electrical contacts 136 of the test strip 104 by the readout device 108. Alternatively, the readout device contacts 144 may comprise two or more flexible wires or leads that can be brought into contact with the electrical contacts 136 of the test strip 104.

In general, the readout device 108 comprises a voltmeter. More particularly, the readout device 108 operates to read a voltage between two readout contacts. Accordingly, the readout device contacts 144 operate to read an electrical potential or a voltage between any two of the electrical contacts 136 of the test strip 104. In accordance with further embodiments, the readout device 108 may perform a galvanostatic measurement, as described in greater detail elsewhere herein. Alternatively, in accordance with embodiments of the present invention, rather than providing three electrical contacts 136, a test strip 104 can include two electrical contacts 136. Similarly, the readout device 108 can include two readout device contacts 144. Moreover, the particular arrangement of readout device contacts 144 and/or readout aperture 148 can vary in order to accommodate different electrical contact 136 and readout region 140 arrangements of different test strips 104.

The readout device 108 may additionally include a user output 152. For example, the user output 152 can comprise a visual display for providing oxidation-reduction potential information regarding the fluid sample 116 to a practitioner. Alternatively or in addition, the user output 152 can comprise a speaker or other source of audible output. In addition, a user input 156 may be provided to allow a practitioner to control aspects of the operation of the readout device 108.

In accordance with embodiments of the present invention, the fluid sample 116 may comprise blood or a blood product. For example, the fluid sample 116 can include human whole blood or plasma. The fluid sample source 112 can comprise any vessel or apparatus suitable for placing an appropriate volume of sample fluid 116 in the sample chamber 120 of the test strip 104. Accordingly, examples of a sample fluid apparatus 112 include a syringe, a lancet, a pipette, a vial or other vessel or device.

Figure 2:
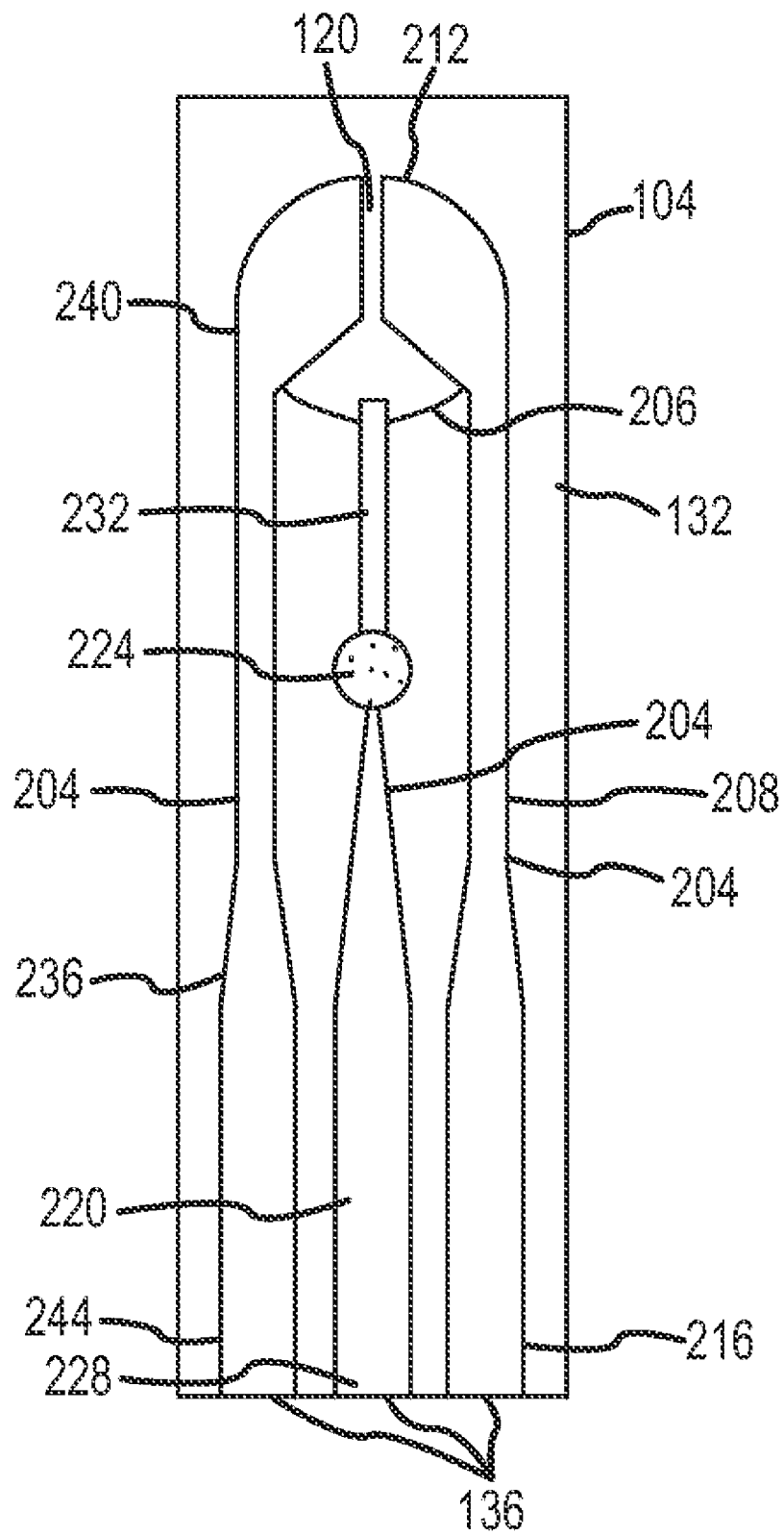
FIG. 2 illustrates components of a test strip in accordance with embodiments of the present invention.

FIG. 2 illustrates components of a test strip 104 with the test strip overlay 128 removed. In general, the substrate 132 carries and/or has formed thereon a number of electrically conductive leads 204 that terminate in the test strip readout contacts 136. The substrate 132 itself may comprise a dielectric material. Moreover, the substrate 132 may comprise a substantially planar surface on which various components of the test strip 104 may be interconnected or formed. In accordance with further embodiments, the test strip 104 substrate 132 may comprise a depression or well 206 in an area corresponding to the sample chamber 120 of the test strip 104.

At least one of the leads 204 is a first test lead or working electrode 208 that extends between a first area 212 corresponding to or within the sample chamber 120 of the test strip 104 and a second area 216 corresponding to the readout contact 136 of the working electrode 208. In accordance with embodiments of the present invention, at least the first area 212 of the working electrode 208 is formed from an electrically conductive material having a substantially continuous and/or uniform composition. It should be understood that, as used herein, a substantially continuous and/or uniform composition means that the material comprising the working electrode 208 has the same chemical composition and/or a molecular structure at any point in a cross section of a portion of the working electrode 208 as at any other point in the cross section of the working electrode 208. More particularly, the electrically conductive material of the working electrode 208 is preferably not coated or substantially not coated by a substance selected to chemically interact with respect to the sample fluid 116.

As examples, and without necessarily importing limitations into the claims, the working electrode 208 may comprise an electrically conductive ink deposited on the substrate 132 in a printing operation. In accordance with further exemplary embodiments, the working electrode 208 may comprise an electrically conductive layer laminated or otherwise joined to the substrate 132.

A test strip 104 in accordance with embodiments of the present invention additionally includes a lead 204 comprising a reference lead or electrode 220. The reference lead 220 generally extends between a reference cell 224 and a readout region of the reference lead 228. In accordance with exemplary embodiments of the present invention, the reference lead 220 may be formed using the same or similar process as the working electrode.

The reference cell 224 is selected to provide a known voltage potential. For example, the reference cell 224 may comprise a silver/silver chloride, copper/copper sulfate, mercury/mercurous chloride, standard hydrogen electrode, or other electrochemical reference half-cell.

A bridge 232 extends between the reference cell 224 and the sample chamber 120. In accordance with embodiments of the present invention, the bridge 232 may comprise a filter. For example, the bridge 232 may be formed from filter paper. As can be appreciated by one of skill in the art after consideration of the present disclosure, when a fluid sample 116 is placed in the sample chamber 120, the filter paper is wetted, establishing an electrically conductive bridge 232 between the fluid sample 116 in the sample chamber 120 and the reference cell 224.

A test strip 104 in accordance with embodiments of the present invention may also include a second test lead or counter electrode 236. The counter electrode 236 may generally mirror the working electrode 208. Accordingly, the counter electrode 236 may be formed from a substantially continuous or uniform electrically conductive substance that extends from a first area 240 that is coincident with the sample chamber 120, to a second area 244 corresponding to the readout portion 136 of the counter electrode 236.

With reference now to FIG. 3, a test strip 104 overlay 128 in accordance with embodiments of the present invention is illustrated in plan view. The test strip 104 overlay 128 includes a test strip aperture 124 corresponding to the sample chamber 120 of the assembled test strip 104. In accordance with embodiments of the present invention, the test strip overlay 128 may comprise a planar piece of dielectric material that is bonded or laminated to the substrate 132 such that the leads 204, reference cell 224, and bridge 232 are held between the substrate 132 and the overlay 128. In accordance with further embodiments of the present invention, a filter or filter element 304 may extend across the test strip aperture 124. The filter 304 may comprise a membrane that functions to allow plasma in a fluid sample 116 comprising whole blood to pass through the test strip aperture to the sample chamber 120. In accordance with at least some embodiments of the present invention, the filter 304 may comprise filter paper. Moreover, in accordance with other embodiments of the present invention, the filter 304 may extend between the sample chamber 120 and the reference cell 224 to form a bridge 232 at least when the filter 304 is wetted.

FIG. 4 illustrates an assembled test strip 104 in accordance with embodiments of the present invention in plan view. Moreover, various features of the test strip 104 that are under the test strip overlay 128 in the assembled test strip 104 are show by dotted lines, to illustrate their relative locations. As can be appreciated by one of skill in the art after consideration of the present disclosure, absent the presence of a suitable fluid sample 116 in the sample chamber 120, the various leads 204 are not in electrical contact with one another. In particular, electrical contact between the leads 204 is not established until a suitable fluid sample 116 is placed in the sample chamber 120, and the bridge 232 has been sufficiently wetted to place the reference lead 220 into electrical contact with the working electrode 208 and/or the counter electrode 236 through the fluid sample 116. Moreover, an electrical circuit including any two of the leads 204 is not completed until the test strip is operatively interconnected to the readout device 108.

Figure 5:
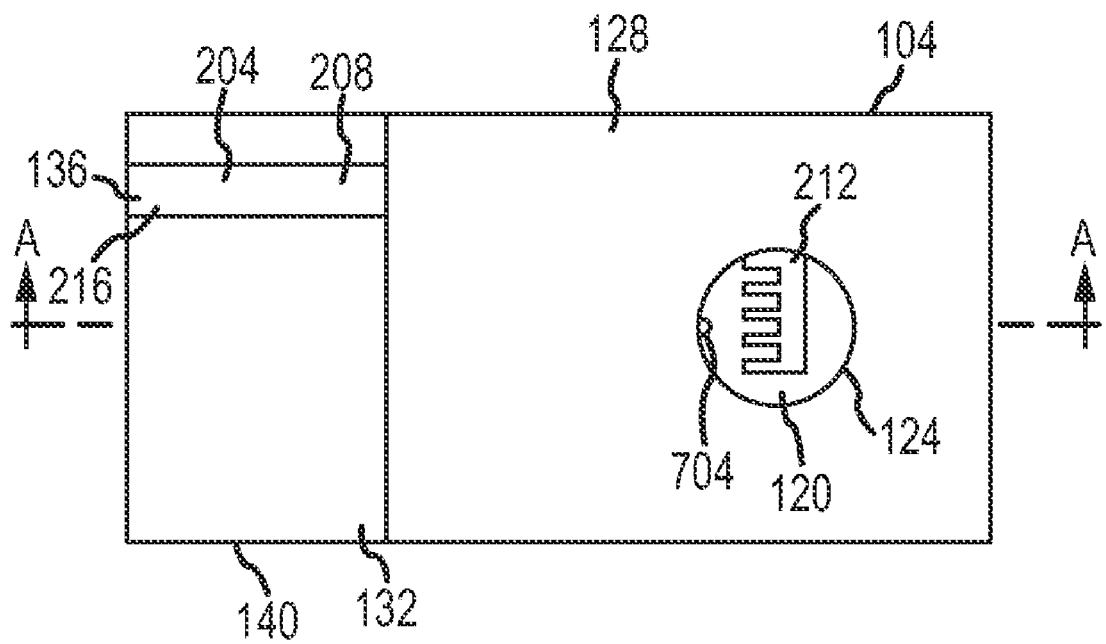
FIG. 5 illustrates a test strip in accordance with other embodiments of the present invention in plan view.

FIG. 5 illustrates a test strip 104 in accordance with other embodiments of the present invention in plan view. The test strip 104 generally includes a substrate 132 with a test strip overlay 128 that covers at least a portion of the substrate 132. The test strip overlay 128 includes a test strip aperture 124 in an area corresponding to a sample chamber 120. As shown, a first area 212 of a test lead 208 extends into the sample chamber 120. A second area 216 of the test lead 208 corresponding to the readout contact 136 is on a portion of the substrate 132 that corresponds to the readout region 140 of the test strip 104, and is not covered by the test strip overlay 128.

Figure 6:
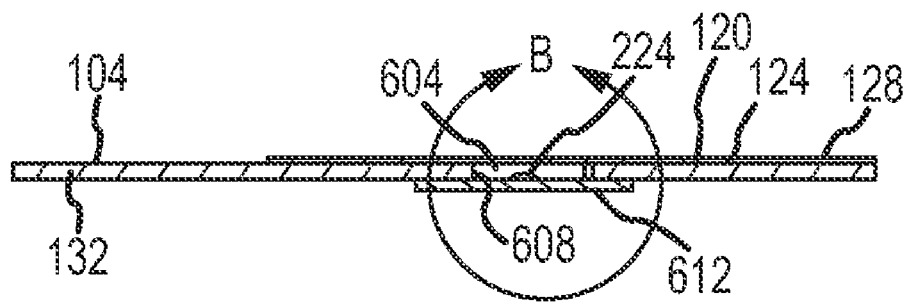
FIG. 6 is a cross-section of the test strip illustrated in FIG. 5, taken along section line A-A.

FIG. 6 is a cross-section of the test strip 104 illustrated in FIG. 5, taken along section line A-A. In this embodiment, the reference cell 224 is contained within a gel volume 604. The gel volume 604 is defined by an aperture 608 formed in the substrate 132. The bottom of the gel volume 604 is bounded by a reference cell carrier plate 612. The top of the gel volume 604 is partially closed by the test strip overlay 128.

Figure 7:
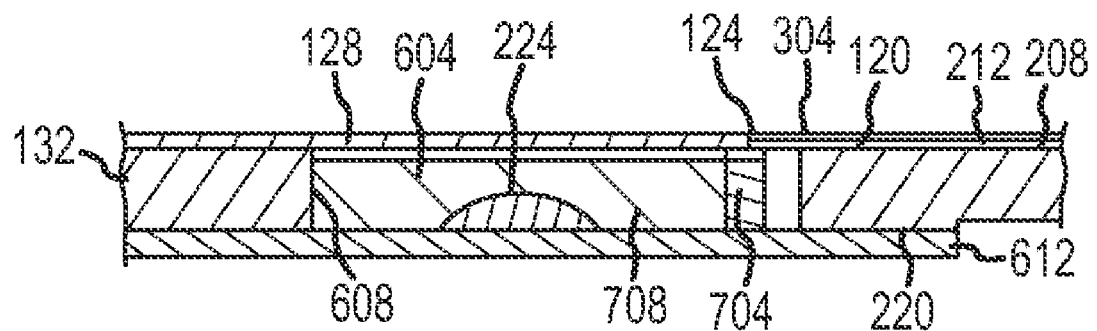
FIG. 7 is a partial cross-section of the test strip illustrated in FIG. 6, taken from within detail area B.

FIG. 7 is a partial cross-section of the test strip 104 illustrated in FIG. 6, taken from within detail area B. As shown in FIG. 7, a notch 704 in the aperture 608 formed in the substrate 132 at least partially overlaps with the test strip aperture 124 formed in the test strip overlay 128. Accordingly, the gel volume 604 is in communication with the sample chamber 120. As a result, at least a portion of a fluid sample 116 placed in the sample chamber 120 can enter the gel volume 604, such that the fluid sample 116 comes into contact with a gel 708. More particularly, the gel 708 at least partially fills the gel volume 604. In accordance with embodiments of the present invention, the gel 708 may comprise an ionic or electrolytic solution. Accordingly, the gel 708 functions to place the fluid sample into electrical contact with the reference cell 224.

With reference again to FIG. 5, it can be seen that the notch 704 in the aperture 608 formed in the substrate 132 and the test strip aperture 124 formed in the test strip overlay 128 cooperate to place the sample chamber 120 in communication with the gel volume 604.

Also visible in FIG. 7 is a filter 304 that covers the sample chamber 120. The filter 304 can be a membrane that separates blood plasma from whole blood placed in or over the sample chamber 120, so that the blood plasma comes into contact with the first area 212 of the test lead 208 and the gel 708 in the gel volume 604. In this exemplary embodiment, the reference lead 220 is on a side of the substrate 132 opposite the side that carries the test lead 208. The reference lead 220 may be placed into electrical contact with the reference cell 224 through electrical contact with an electrically conductive carrier plate 612.

Figure 8:
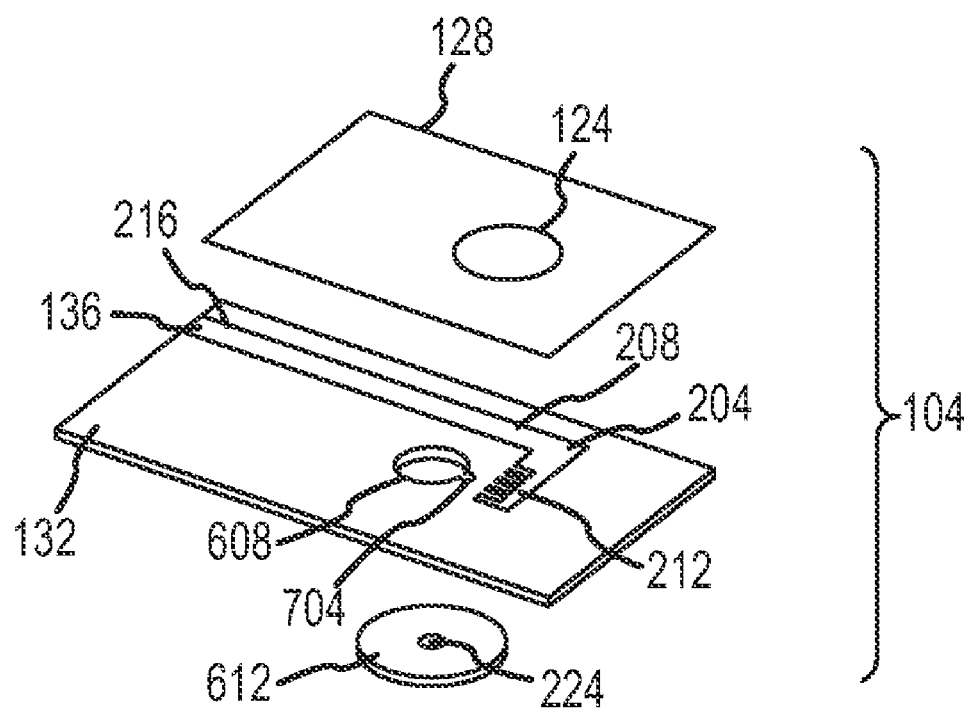
FIG. 8 is an exploded view of the test strip illustrated in FIG. 5.

FIG. 8 is an exploded view of the test strip 104 illustrated in FIG. 5. In this exploded view, it can be seen that the working electrode 208 is formed on the substrate 132, and extends from the first area 212 to the second area 216. In addition, in this embodiment the reference cell 224 is centered on an electrically conductive reference cell carrier plate 612.

Figure 11:
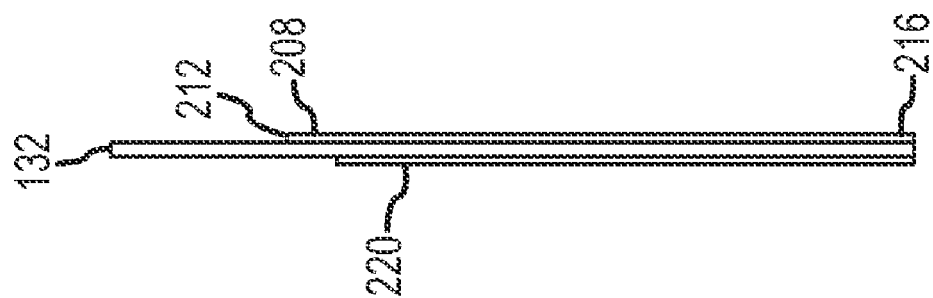
FIG. 11 is a view of the test strip substrate shown in FIG. 5 in elevation in accordance with embodiments of the present invention.
Figure 10:
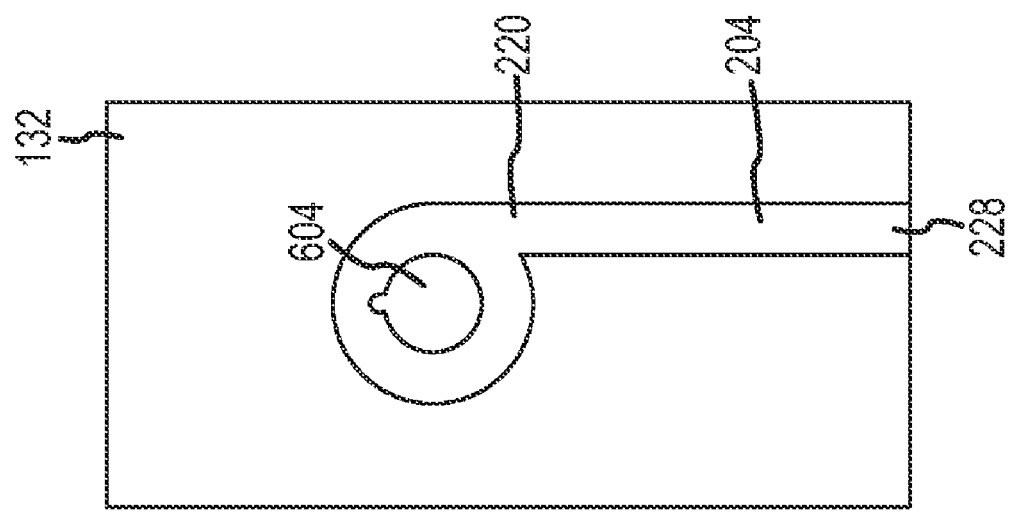
FIG. 10 is a bottom plan view of the test strip substrate shown in FIG. 5 in accordance with embodiments of the present invention.
Figure 9:
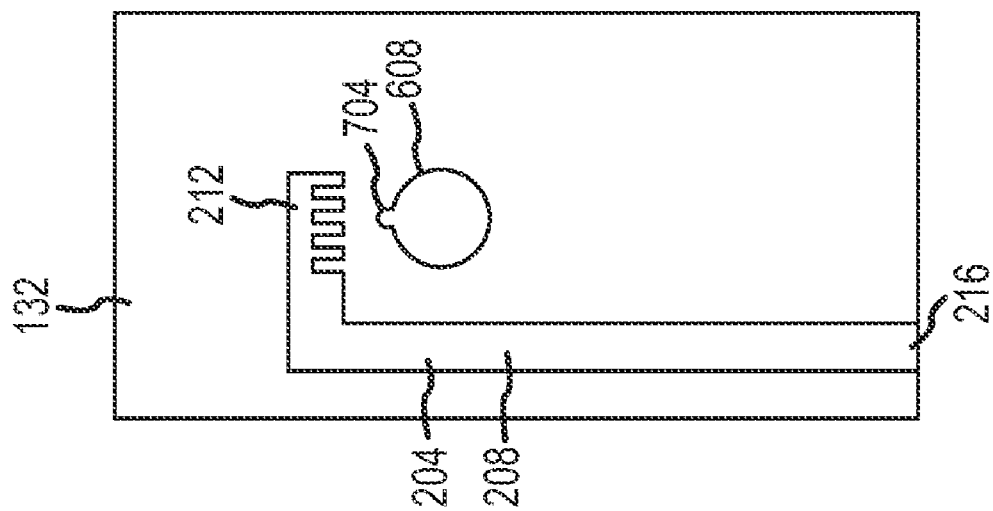
FIG. 9 is a top plan view of the substrate of the test strip shown in FIG. 5 in accordance with embodiments of the present invention.

FIG. 9 is a top plan view of the substrate 132 of the test strip 104 shown in FIG. 5, FIG. 10 is a bottom plan view of that test strip substrate 132, and FIG. 11 is a view of that test strip substrate 132 in elevation. As shown in FIG. 9, the aperture 608 in the substrate 132 may be circular, with a notch 704 formed in a periphery thereof. FIG. 10 shows the reference lead 220 that is formed on a side of the substrate 132 opposite the side carrying the working lead 208. In particular, the reference lead 220 can include a circular portion that surrounds an area outside of the gel volume 604. Moreover, the test lead 208 and the reference lead 220 may be formed on opposite sides of the substrate 132 (see FIG. 11).

Figure 12:
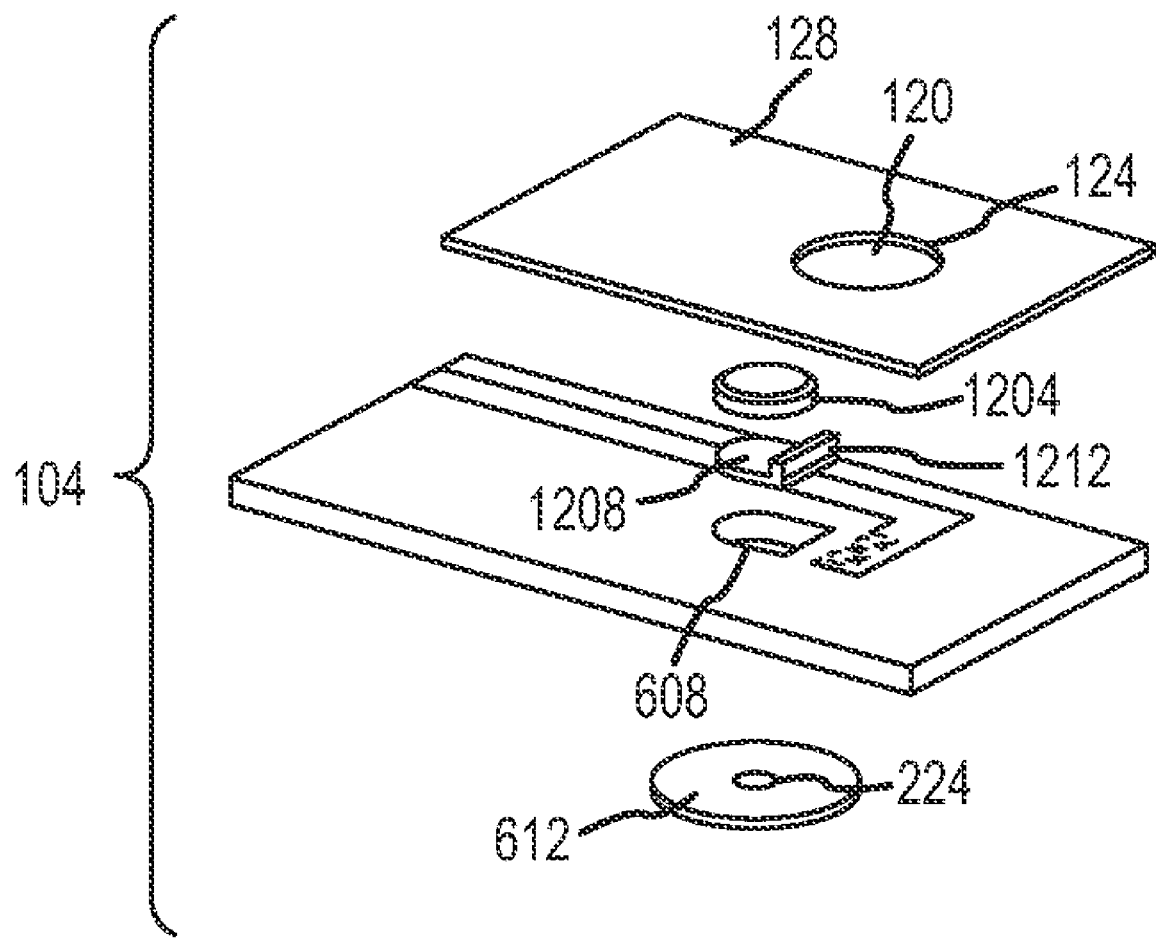
FIG. 12 is an exploded view of a test strip in accordance with further embodiments of the present invention.

With reference now to FIG. 12, an exploded view of a test strip 104 in accordance with further embodiments of the present invention is illustrated. In particular, this embodiment includes a capsule 1204 that contains an ionic gel or other electrolyte. A wicking member 1208 is placed under the capsule 1204. The wicking member 1208 includes a tab 1212 that is in communication with the sample chamber 120. In use, the capsule 1204 is broken, wetting the wicking member 1208 and thereby establishing a salt bridge between the reference cell 224 and a sample fluid 116 in the sample chamber 120. In the assembled test strip 104, the gel capsule 1204 and the wicking member 1208 are held within an aperture 608 formed in the substrate 132, between the test strip overlay 128 and the reference cell carrier plate 612.

Figure 13:
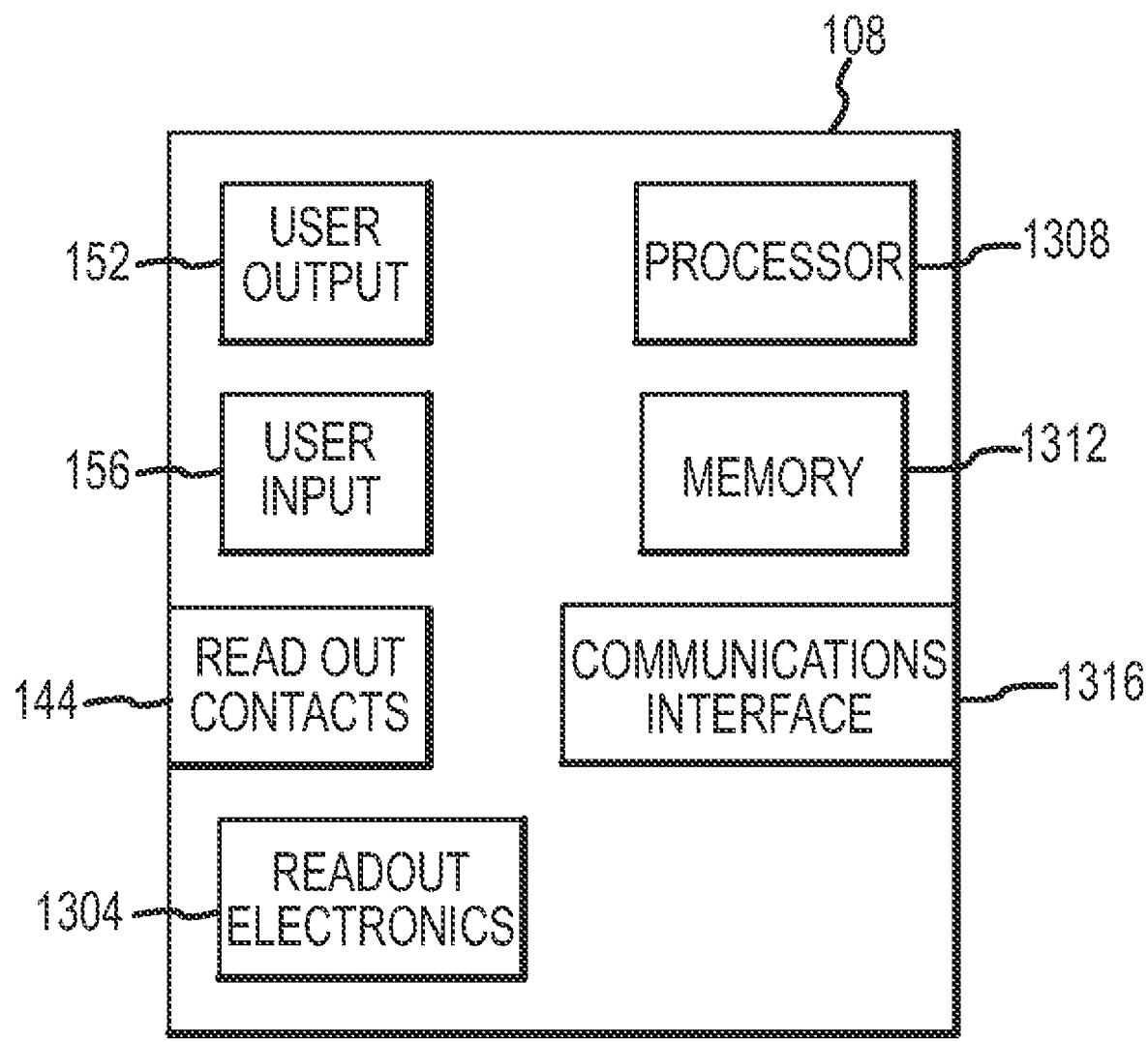
FIG. 13 is a block diagram depicting components of a readout device in accordance with embodiments of the present invention.

FIG. 13 is a block diagram depicting components of a readout device 108 in accordance with embodiments of the present invention. In general, the readout device 108 includes a plurality of readout device contacts 144. The readout device contacts 144 may be associated with a receiving structure, such as the aperture 148 illustrated in FIG. 1, for mechanically interconnecting the readout device 108 to a test strip 104, to facilitate an electrical interconnection between at least two readout device contacts 144 and at least two electrical contacts 136 of the test strip 104. Alternatively or in addition, the readout device contacts 144 may comprise conductive leads or probes that can be selectively placed into contact with electrical contacts 136 of a test strip 104.

The readout device 108 also includes or comprises a voltmeter or readout electronics portion 1304. As can be appreciated by one skilled in the art, the readout electronics 1304 can be implemented in various ways. For example, the readout electronics 1304 may comprise a galvanostat. As another example, the endpoint electronics may comprise a potentiostat. As a further example, the readout electronics 1304 may comprise a digital voltmeter that includes an integrating converter. In accordance with further embodiments, the readout electronics 1304 can comprise an analog voltmeter or a digital or analog null balance voltmeter.

A processor 1308 that includes and/or is associated with memory 1312 can be provided for controlling various aspects of the operation of the readout device 108. The processor 1308, for example executing instructions stored in memory 1312, can implement a process according to which the voltage between the working electrode 208 (or alternatively the counter electrode 236) and the reference electrode 220 is monitored over time by the readout electronics 1304. Moreover, this voltage can be monitored while the readout electronics 1304 applies a current across at least the counter electrode 236 and the working electrode 208. The processor 1308 can further operate to calculate and cause to be displayed a readout indicative of the oxidation-reduction potential of a fluid sample 116 held in the sample chamber 120 from the voltage read by the readout electronics 1304.

For providing information regarding the determined oxidation-reduction potential of a fluid sample 116 in the sample chamber 120 to a user, a user output 152 is provided. The user output 152, can, in an exemplary embodiment, comprise a digital output that displays an oxidation-reduction potential value. Alternatively or in addition, the user output 152 can include indicator lamps, an analog output, or other visually discernable output. In accordance with still further embodiments, the user output 152 can include an audible output, such as a selected tone or sequence of tones or machine-generated speech.

A user input 156 can be included for receiving control information from a user. For example, the user input 156 may receive input to power on or power off the readout device 108, to perform diagnostics related to the proper operation of the readout device 108, to receive input regarding various operating parameters, or other user input. As examples, the user input 156 can include buttons, switches, keypads, and/or a touch screen interface integrated with a visual display, such as may be included in the user output 152.

The readout device 108 may additionally include a communications interface 1316. The communications interface 1316, if provided, may support interconnections between the readout device 108 and other systems or devices. For example, the communications interface 1316 may comprise a wired or wireless Ethernet connection, a universal serial bus port, or an IEEE 1394 port for interconnecting the readout device 108 to a personal computer or computer network.

In addition, although an exemplary readout device 108 comprising a dedicated standalone device that may or may not be interconnected to other devices has been described, embodiments of the present invention are not so limited. For example, a readout device 108 in accordance with embodiments of the present inventions may be implemented as a standard voltmeter. In accordance with other embodiments, the readout device 108 may comprise an electrical test or diagnostic system, such as a user configurable potentiostat and/or galvanostat operated alone or in combination with a personal computer. In accordance with still other embodiments, a readout device 108 may be implemented as a personal computer running suitable programming and providing an interface capable of sensing a voltage between a working electrode 208 and a reference electrode 220 of a test strip 104.

Figure 14:
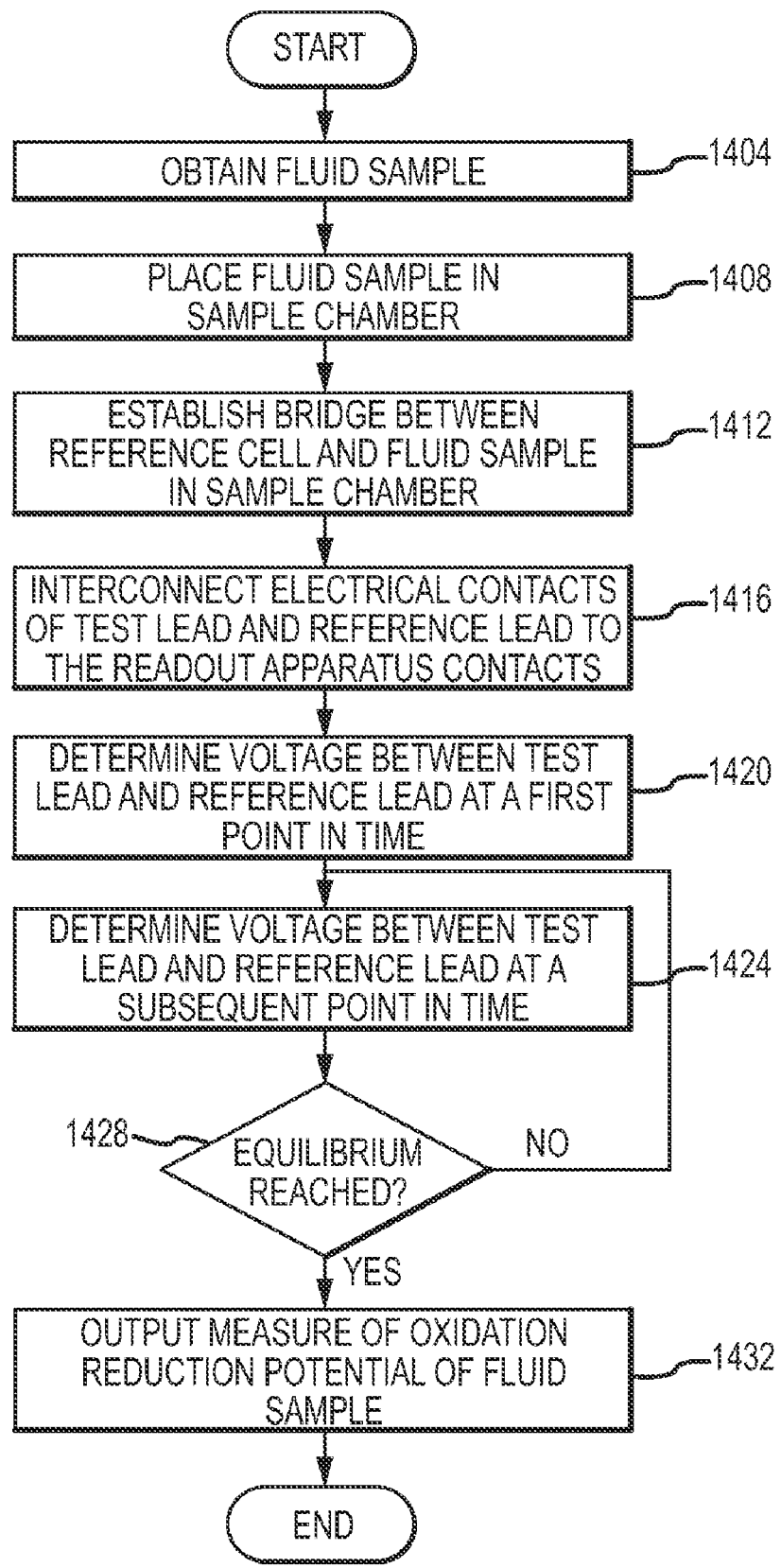
FIG. 14 is a flow chart depicting aspects of a process for measuring the oxidation-reduction potential of a fluid sample in accordance with embodiments of the present invention.

FIG. 14 illustrates aspects of a method for determining the oxidation-reduction potential of a fluid sample 116 in accordance with embodiments of the present invention. Initially, at step 1404, a fluid sample 116 is obtained from a test subject or patient. In accordance with embodiments of the present invention, the fluid sample 116 comprises whole blood or a blood product, such as plasma. As can be appreciated by one skilled in the art, a fluid sample 116 comprising whole blood or a blood product can be obtained from a test subject, for example using a syringe and needle or a lancet. In accordance with further embodiments, the fluid sample can include any fluid from a living test subject. Moreover, a test subject can include a human or any other mammal or animal.

At step 1408, the fluid sample 116 is placed in the sample chamber 120 of a test strip 104. Where the fluid sample 116 comprises plasma, the plasma may be separated from the whole blood in a separate process. Alternatively, where the sample fluid 116 comprises whole blood, a filter 304 over the sample chamber 120 may operate to filter other components of the whole blood from a plasma component. The plasma component of the fluid sample 116 is then allowed to collect in the sample chamber 120 or a portion of the sample chamber 120.

At step 1412, an electrically conductive bridge 232 between the reference cell 224 and the sample chamber 120 is established. In accordance with at least some embodiments of the present invention, this can be accomplished by wetting a bridge 232 formed using at least a portion of a filter 304 comprising a strip of filter paper, thereby establishing a salt bridge connection between the sample chamber 120 and the reference cell 224. In accordance with other embodiments, this can be accomplished by placing the fluid sample 116 in contact with an electrolytic gel that is also in contact with the reference cell 224, either directly or in connection with a filter 304 and/or a bridge 232. At step 1416, the test lead 208 and the reference lead 220 are interconnected to the electrical contacts 144 of a readout device 108. At step 1420, the voltage or electrical potential between the working electrode or test lead 208 and the reference electrode 220 is determined. After a selected interval has elapsed, a subsequent reading of the voltage between the working electrode or test lead 208 and the reference cell electrode 220 is taken (step 1424). At step 1428, a determination is made as to whether the rate of change between the two readings indicates that the system has reached equilibrium and therefore that a reliable reading has been obtained. If it is determined that the system has not reached equilibrium, the system returns to step 1424, and a further subsequent reading of the voltage between the working electrode 208 and the reference cell electrode 220 is taken. If it is determined at step 1428 that the system has stabilized, the measure of the oxidation-reduction potential of the fluid sample 116 in the sample chamber 120 can be output (step 1432). For example, an indication of the oxidation-reduction potential of the fluid sample 116 can be output through the user output 152 and/or output to another device through a communications interface 1316.

In accordance with still other embodiments, a curve fitting procedure may be performed in order to determine the oxidation-reduction potential of the sample 116. For example, the voltage between the working electrode 208 and the reference cell electrode 220 can be taken at at least three different points in time, and the data thus obtained can be applied to a curve fitting algorithm to arrive at an oxidation-reduction potential reading. The curve fitting algorithm may comprise a diffusion equation, a polynomial curve fitting algorithm, or any other curve fitting algorithm.

In accordance with embodiments of the present invention, a test strip 104 may be formed using a substrate 132 that comprises any dielectric material capable of providing mechanical support to the leads 204 and other components. Accordingly, the substrate 132 may comprise plastic, ceramic, glass, or other material. Moreover, the substrate 132 may comprise a planar sheet of material. The leads 204 may be formed through various means. For example, the leads 204 may be deposited as a conductive ink on the substrate 132. Examples of suitable conductive ink include graphite inks and noble metals, such as gold, platinum or iridium. Leads 204 may also be formed through various other deposition and/or etching processes. Moreover, the reference cell 224 and bridge 232 may be applied by placing appropriate materials on the substrate 132.

The test strip overlay 128 may comprise the same or a similar material as the substrate 132. Moreover, the test strip overlay 128 can include a test strip aperture 124 corresponding to the sample chamber 120. The test strip overlay 128 may be bonded to the substrate 132, such that some or all of the other components, such as the leads 204, reference cell 224 and bridge 232, are at least partially held between a substantially planar top surface of the substrate 132 and a substantially planar bottom surface of the test strip overlay 128.

The reference cell 224 may comprise any chemical half cell or electrode that is capable of providing a known reference voltage. Accordingly, the reference cell 224 may comprise a standard hydrogen electrode, a silver/silver chloride electrode, a calomel electrode, a mercurous sulfate electrode, a mercuric oxide electrode, or a copper/copper sulfate electrode. In embodiments of a test strip 104 incorporating a gel 708, that gel 708 may comprise any ionic liquid, electrolytic solution or ionic gel. Examples of suitable gels 708 include cationic polymers, ionic liquids, and gelled electrolytes.

Figure 15:
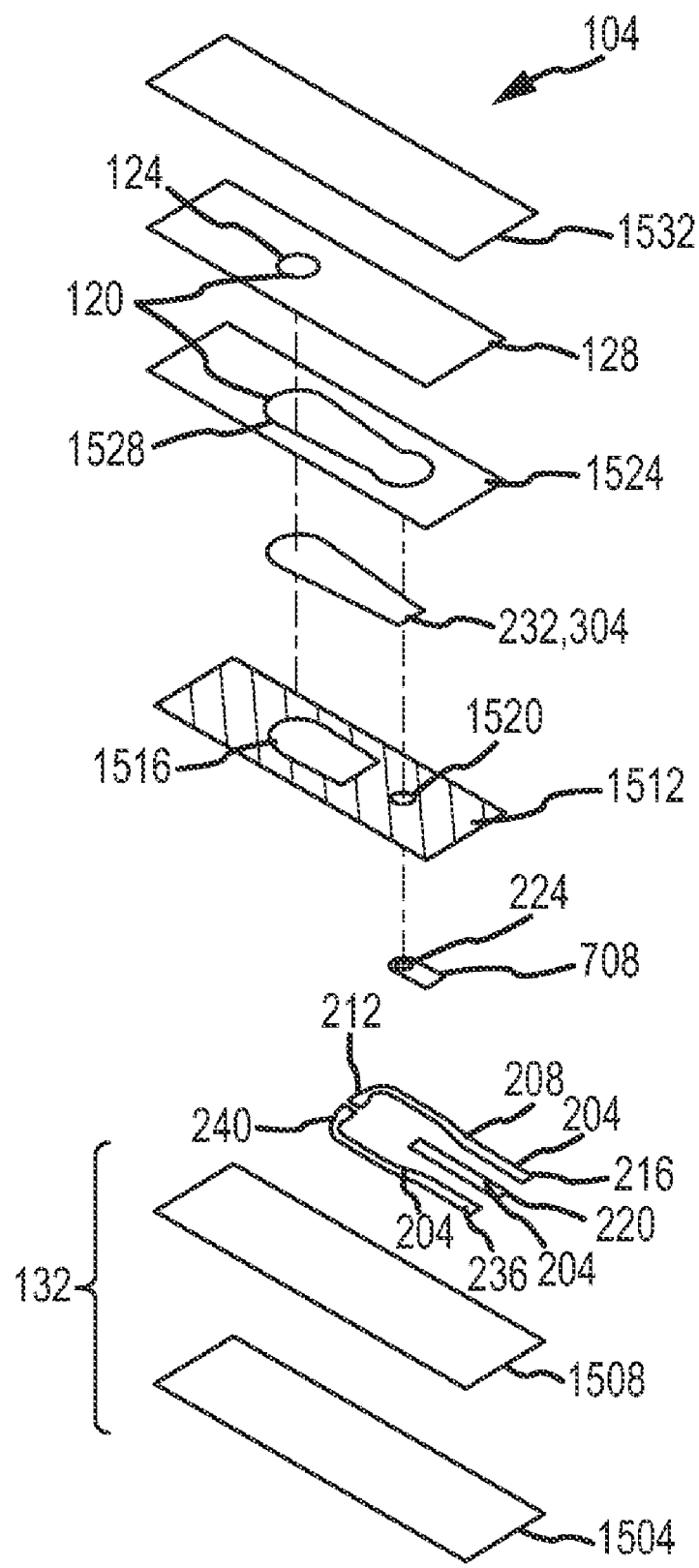
FIG. 15 is an exploded elevation view of a test strip in accordance with other embodiments of the present invention.
Figure 16:
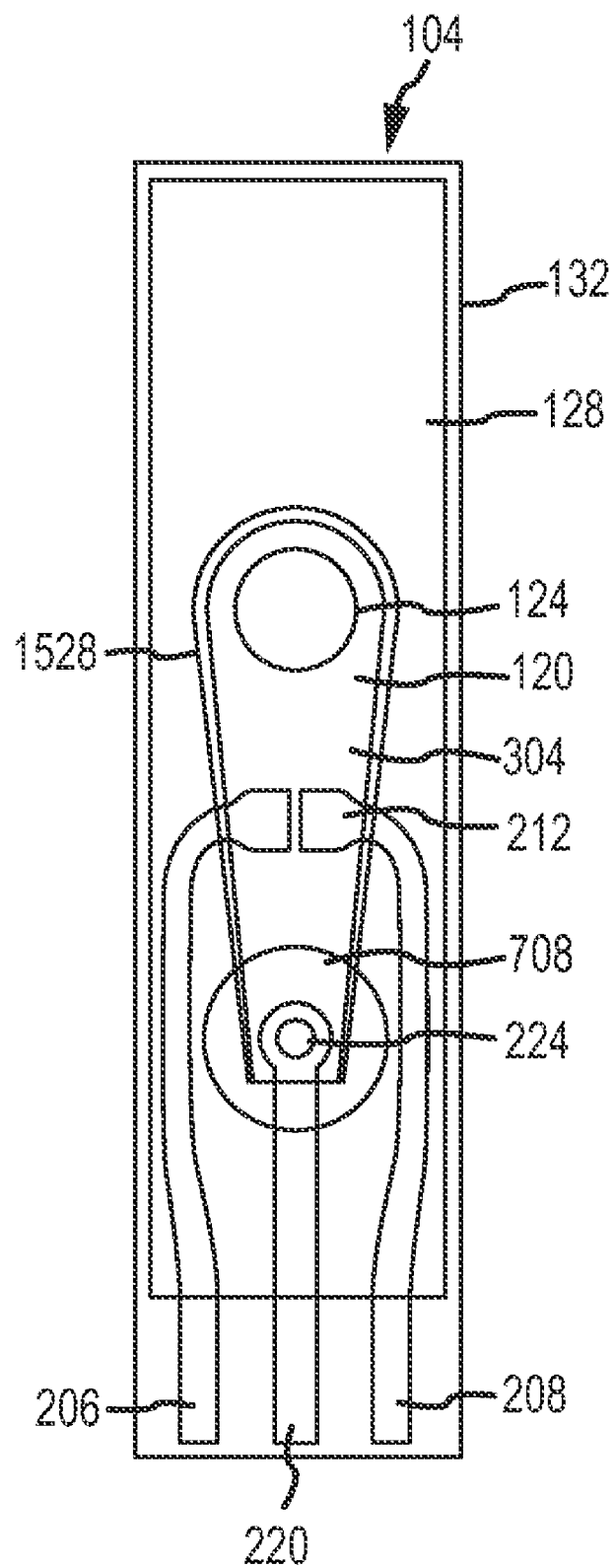
FIG. 16 is a top plan view of the test strip according to FIG. 15.

A further embodiment of the present invention is now described with reference to FIGS. 15 and 16. FIG. 15 illustrates an exploded view of a test strip 104 in accordance with embodiments of the present invention. FIG. 16 illustrates the test strip 104 of FIG. 15 in the top plan view. The test strip 104 includes a substrate 132. More particularly, the substrate 132 in this exemplary embodiment includes a structural support layer 1504 and a barrier layer 1508. The barrier layer 1508 may comprise a layer that is impermeable to liquids. For example, the barrier layer 1508 may comprise an oriented polyester film, such as but not limited to, a biaxially-oriented polyethylene terephthalate, such as Mylar™. The structural support layer 1504 may comprise a fiber or polymer layer that is sufficiently rigid to provide mechanical support for the subsequent layers, such as but not limited to a polyester material.

Electrically conductive leads 204 are supported by the barrier layer 1508. As an example, and without limitation, the conductive leads 204 can be deposited on the surface of the barrier layer 1508 by a sputtering, printing, etching, stenciling, or plating process. The electrically conductive leads 204 may be formed from any electrically conductive material. Examples of suitable electrically conductive materials include platinum, gold and doped carbon. The conductive leads 204 can be formed in various patterns. In general, the conductive leads 204 include a working electrode 208, a reference electrode 220 and a counter electrode 236.

A reference cell 224 can be placed within a gel 708 deposited on the barrier layer 1508. Moreover, at least some of the gel 708 is placed over or in contact with a portion of the reference lead or electrode 220. A dielectric layer 1512 may be placed over or formed on portions of the barrier layer 1508. For example, the dielectric layer 1512 can cover portions of the various electrically conductive leads 204, while leaving portions of the electrically conductive leads 204 corresponding to a readout region 140 of the electrically conductive leads 204 uncovered. In addition, the dielectric layer 1512 can include a first aperture 1516 that leaves a first area 212 of the working electrode 208 and a first area 240 of the counter electrode 236 uncovered and exposed to a volume corresponding to a sample chamber 120. The dielectric layer 1512 can additionally include a second aperture 1520. The second aperture 1520 can correspond to the reference cell 224 and/or the gel 708. As an example, the dielectric layer 1512 may be formed from a dielectric film, or a deposited (e.g., a printed) dielectric material.

A filter 304 is provided that extends from an area encompassing at least part of the first aperture 1516 and the second aperture 1520 of the dielectric layer 1512. As with other embodiments described herein, the filter 304 can function, when wetted, as a bridge 232 to electrically connect a portion of a sample 116 within the sample chamber 120 to the reference cell 224, directly or through the gel 708.

A spacer layer 1524 is interconnected to the dielectric layer 1512. The spacer layer 1524 includes a spacer layer aperture 1528. The spacer layer aperture 1528 may have an area that is the same as or larger than an area of the filter 304. Accordingly, the spacer layer aperture 1528 can define the perimeter of a volume that is entirely or substantially occupied by the filter 304.

Next, a test strip overlay 128 can be interconnected to the spacer layer 1524. The test strip overlay 128 generally includes an overlay aperture 124. In general, the overlay aperture 124 cooperates with the spacer layer 1524 aperture 1528 to define portions of a sample chamber 120.

In accordance with embodiments of the present disclosure, the structural support layer 1504 and the barrier layer 1508 have the same or substantially similar lengths and widths, and are adhered or bonded to one another to form the laminated substrate 132. The dielectric layer 1512, spacer layer 1524, and test strip overlay layer 128 have the same or a similar length and width as one another, and a length that is less than the length of the laminated substrate 132. Accordingly, the dielectric layer 1512, spacer layer 1524, and test strip overlay layer 128 leave a readout region 140 of the test strip 104 electrically conductive leads 204 uncovered.

A test strip 104 in accordance with embodiments of the present invention can additionally include a protective layer 1532. The protective layer 1532 may have a length and width that is the same or similar to the length and width of the substrate 132, to cover the top surface of the test strip 104 (i.e., the surface of the test strip 104 opposite the substrate 132) in its entirety. Accordingly, the protective layer 1532 is removed from the test strip 104 before use. The protective layer 1532 can comprise a sealer film, such as a polymeric material.

At least one of the leads 204 is a working electrode or first test lead 208 that extends between a first area 212 corresponding to or within the sample chamber 120 and a second area 216 corresponding to the readout contact 136 of the working electrode 208. Another lead 204 comprises a reference lead 220. The reference lead 220 extends between the reference cell 224 and a readout region of the reference lead 228. Moreover, in accordance with embodiments of the present invention the test strip 104 may optionally include a second test lead or counter electrode 236. The counter electrode 236 may generally mirror the working electrode 208.

In accordance with embodiments of the present invention, at least some, if not most or all, of the leads 204 are formed by printing an electrically conductive material. Non-limiting examples of electrically conductive materials are carbon (such as carbon black, carbon nanotubes, graphene sheets, graphite and bucky balls), metallic materials (such as powder forms of copper, silver, gold and other known conductive metallic materials) and conductive polymers. Furthermore, the conductive material is printed in the form of a substantially continuous and/or uniform composition, as described above. In accordance with further embodiments, the leads 204 are formed by sputtering gold, platinum, or some other metal.

A top plan view of the test strip 104 illustrated in FIG. 15 is shown in FIG. 16. In this view, the sealer film 1532, test strip overlay 128, spacer 1524, filter 304, and dielectric layer 1512 are depicted as being transparent, so that the relative positions of various components of the test strip 104 can be seen.

The test strip 104 forms an electrochemical test cell. In particular, when a blood sample has been placed in the sample cell 120, for example through the test strip overlay layer 128 aperture 124, the electrochemical test cell comprises the separated plasma, contained within the sample chamber 120 and wetting the filter 304, the gel 708, and the reference cell 224. The electrical potential of the test cell can then be read by interconnecting at least one of the working electrode 208 and counter electrode 236, and the reference lead 220 to a readout apparatus or device 108.

Figure 17:
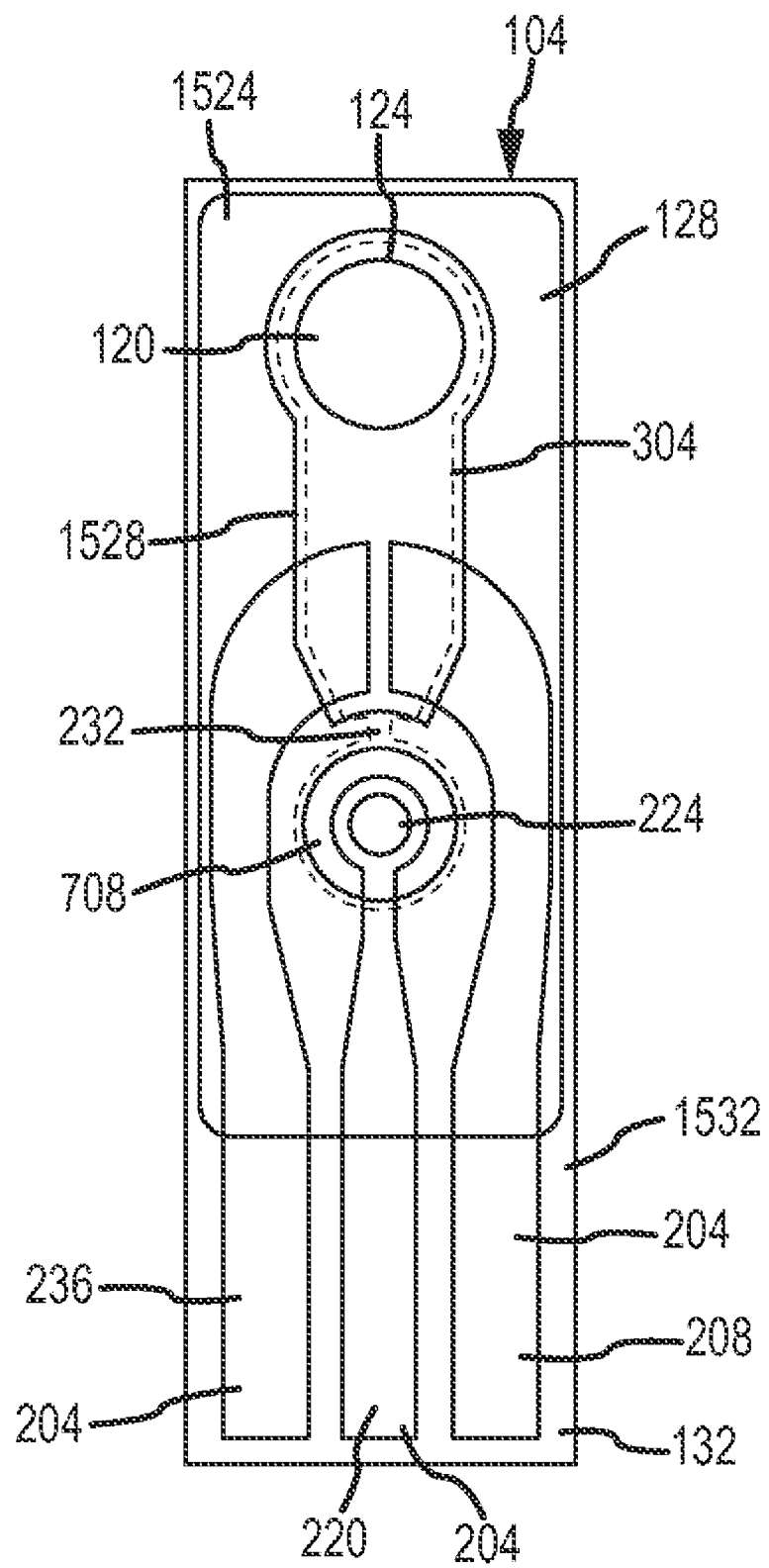
FIG. 17 is a top plan view of a test strip in accordance with further embodiments of the present invention.

FIG. 17 illustrates an example of a test strip 104 in accordance with other embodiments of the present invention in top plan view. In this example, the sealer film 1532, test strip overlay 128, spacer 1524, filter 304, and dielectric layer 1572 are depicted as being transparent, so that the relative positions of various components of the test strip 104 can be seen. The filter 304 extends from the sample chamber 120 to an area including a gel 708. The reference cell 224 in this embodiment comprises a Ag/AgCl half cell that is surrounded by a hydroxyethyl cellulose gel 708. In addition, at least a portion of the reference cell 224 may be in direct contact with the reference lead 220. The electrically conductive leads 204 can comprise sputtered gold and/or sputtered platinum. The use of sputtered metal can provide a more uniform surface than a conductive ink. Alternatively, the electrically conductive leads 204 can be formed from electrically conductive ink. As an example, the electrically conductive leads 204 can be deposited in a layer that is about 5,000 Angstroms thick.

In accordance with embodiments of the present invention, the procedure for applying the gel 708 over the reference cell 224 can be controlled, in order to obtain more consistent results. For example, the gel 708 can be dried under conditions that limit or reduce the formation of microcracks or other discontinuities. Accordingly, drying the gel 708 can be performed at ambient temperatures and pressures, while applying heat, in a vacuum, and the like. As an alternative to a dried gel 708, a gel 708 can be contained within a capsule, which is broken immediately prior to use of the test strip 104. Alternatively or in addition, different gel 708 compositions can be used. For example, a gel comprising a hydroxyethyl cellulose material can be mixed with a polymer to promote consistency of the gel 708 in finished test strips 104.

Figure 18:
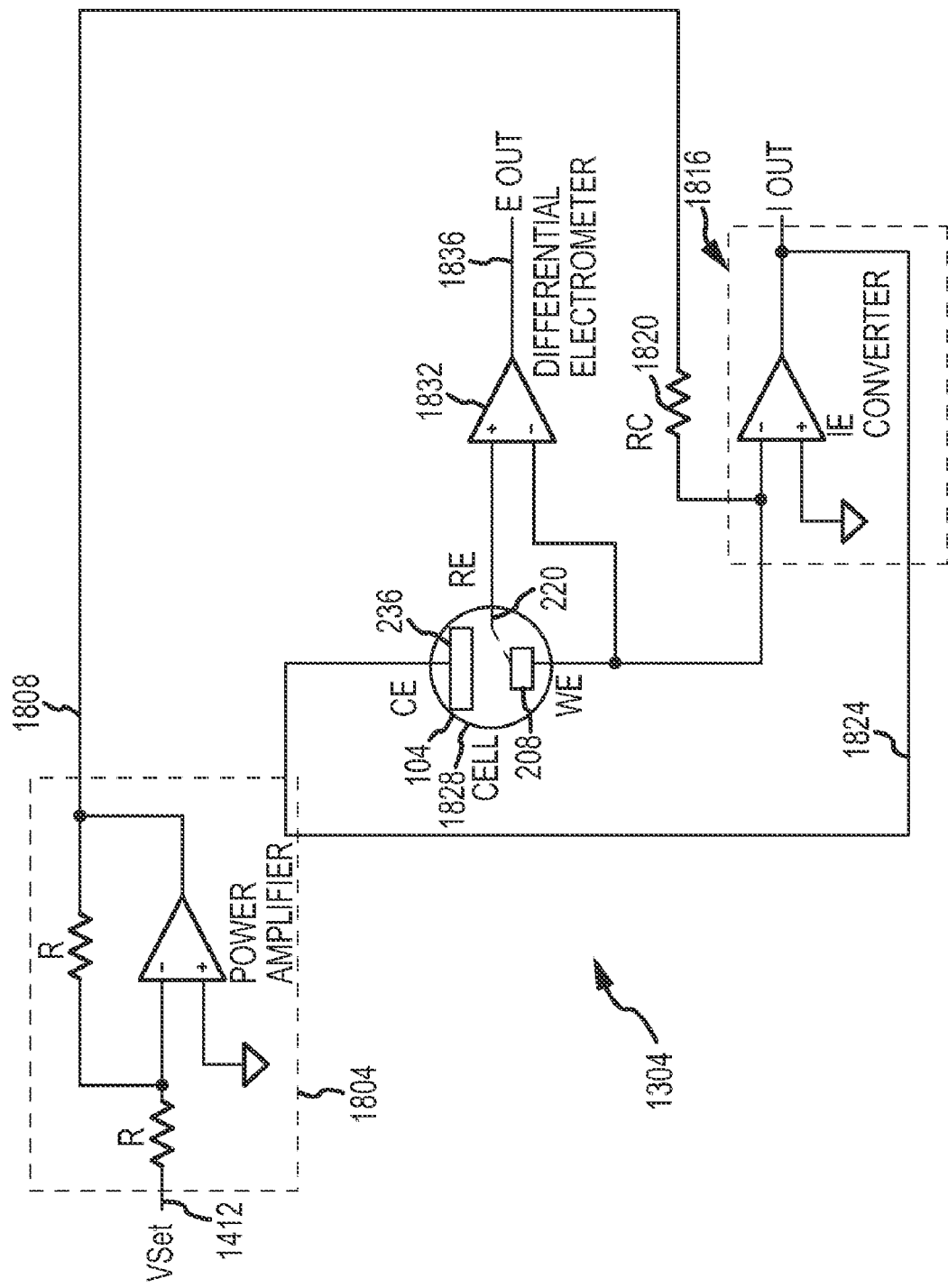
FIG. 18 depicts components of readout electronics 1304 and an interconnected test strip 104 in accordance with embodiments of the present invention.

FIG. 18 depicts components of a readout device 108 operatively interconnected to a test strip 104 in accordance with embodiments of the present invention. More particularly, features of a voltmeter or readout electronics portion 1304 of a readout device 108 interconnected to a test strip 104 containing a fluid sample 116 are depicted. As can be appreciated by one of skill in the art after consideration of the present disclosure, the test strip 104 containing a fluid sample 116 comprises an electrochemical cell 1828. The electrochemical cell 1828 includes the fluid sample 116, the electrolytic gel 708 (if provided), and the reference cell 224. Moreover, the fluid sample 116, for example by wetting a bridge 232 and/or filter 304, places portions of the working electrode 208, reference electrode 220, and counter electrode 236 in electrical contact with one another.

In general, the readout electronics 1304 include a power amplifier 1804. The output 1808 from the power amplifier 1804 comprises a current having a set point determined by the voltage $V_{set}$ 1812 provided as an input to the power amplifier 1804. The output current 1808 from the power amplifier 1804 is passed to a current-potential (IE) converter 1816. The current 1808 from the power amplifier 1804 can be supplied via a resistor 1820 to the negative input of the IE converter 1816. The IE converter 1816 in turn supplies an output current 1824 that is provided to the counter electrode 236. The negative input of the IE converter 1816 is additionally connected to the working electrode 208. As can be appreciated by one of skill in the art after consideration of the present disclosure, the resistance between the counter electrode 236 and the working electrode 208 can vary, depending on the composition and characteristics of a fluid sample 216 placed in the test strip 104. However, the power amplifier 1804 and the IE converter 1816, in combination, provide a constant current that is supplied to the counter electrode 236, and that is passed through the electrochemical cell 1828.

While the current is applied across the counter electrode 236 and the working electrode 208, the voltage potential between the working electrode 208 and the reference electrode 220 is monitored by a differential amplifier or electrometer 1832. More particularly, the differential amplifier 1832 provides a voltage output 1836 that is indicative of the oxidation-reduction potential of the sample 116 placed within the sample chamber 120. This voltage output 1836 can be presented to a user, for example through the output 152 of the associated readout device 108.

Figure 19:
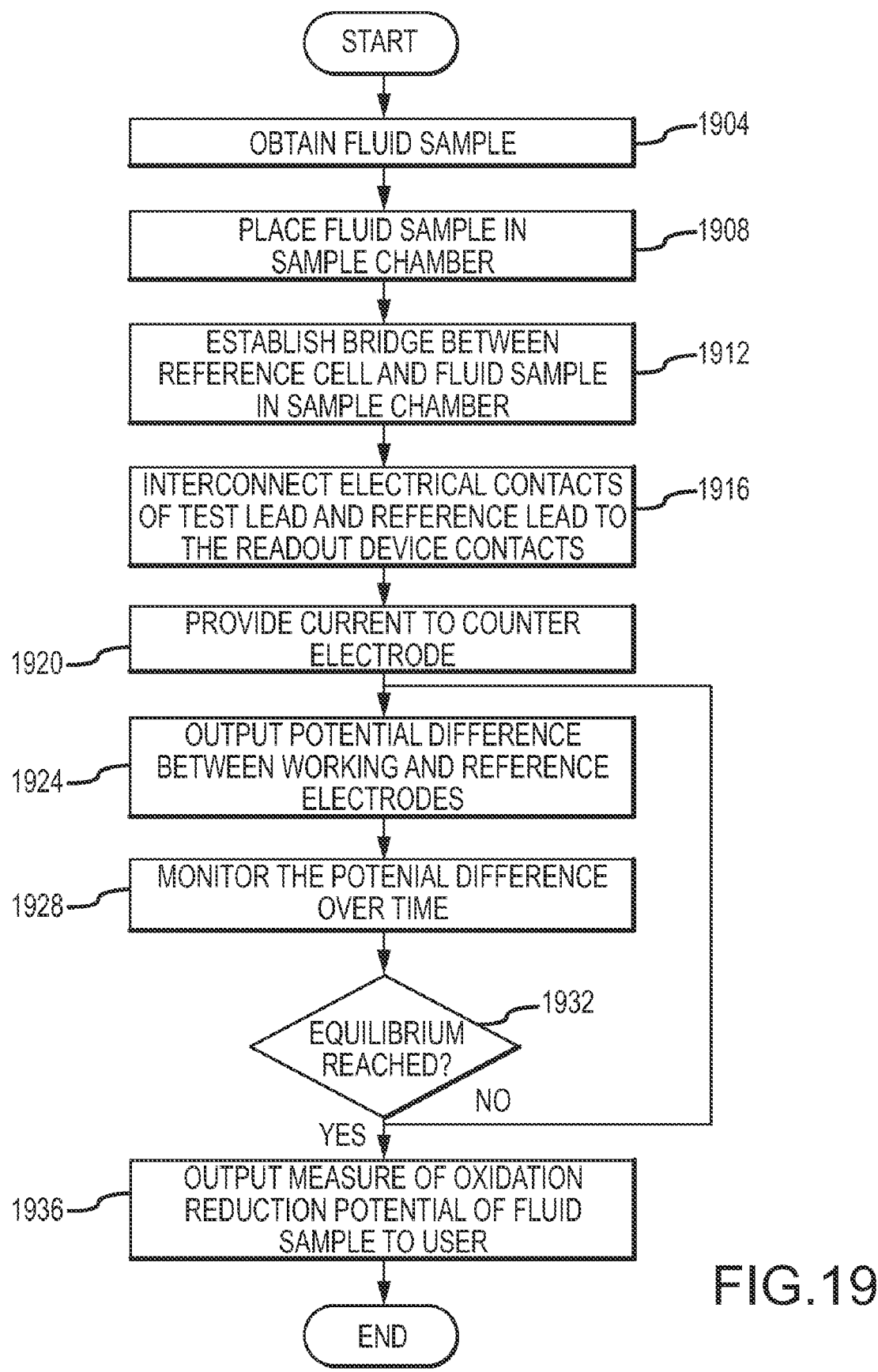
FIG. 19 is a flowchart depicting aspects of a process for measuring the oxidation-reduction potential of a fluid sample in accordance with other embodiments of the present invention.

With reference now to FIG. 19, aspects of a method for measuring the oxidation-reduction potential (ORP) of a sample fluid 116 are illustrated. In general, the method includes steps of obtaining a fluid sample 116 (step 1904), placing the fluid sample 116 in the sample chamber 120 of a test strip 104 (step 1908), and establishing an electrically conductive bridge 232 between the reference cell 224 and the sample chamber 120 of the test strip 104, for example by wetting a filter 304 with the sample fluid 116 (step 1912). Accordingly, steps 1904 to 1912 are the same or similar as steps 1404 to 1412 described in connection with FIG. 14 above.

At step 1916, the working electrode 208, reference electrode 220, and counter electrode 236 are interconnected to readout device contacts 144. For example, the counter electrode 236 can be interconnected to the current output 1824 of the readout electronics 1304, the working electrode 208 can be connected to the negative inputs of the IE converter 1816 and the differential electrometer 1836 of the readout electronics 1304 and the reference electrode 220 can be interconnected to an input of the differential amplifier 1832. The readout electronics 1304 are then operated to provide a current that is passed across the reference cell 1828, between the counter electrode 236 and the working electrode 208 (step 1920). As examples, and without limitation, the amount of current passed between the counter electrode 236 and the working electrode 208 by the readout electronics 1304 can be from about $10^{-12}$ amps to about $10^{-9}$ amps. In accordance with further embodiments, the magnitude of the current passed through the electrochemical cell 1828 can be from about $1 \times 10^{-14}$ amps to about $1 \times 10^{-6}$ amps. As further examples, the applied current can be varied over time. For instance, a step function can be followed, according to which the applied current changes after some point of time from a first value (e.g., $10^{-9}$ amps) to a second value (e.g., $10^{-11}$ amps). While the current is applied between the counter electrode 236 and the working electrode 208, the potential difference between the working electrode 208 and the reference electrode 220 is provided as the output 1836 of the differential amplifier 1832 (step 1924).

The output 1836 from the differential amplifier 1832 can be monitored over time (step 1928). At step 1932, a determination can be made as to whether equilibrium has been reached. The determination that equilibrium has been reached can include monitoring the rate of change in the output signal 1836 of the differential amplifier 1832, until that rate of change has dropped to a predetermined level. Alternatively, the output voltage 1836 can be measured at different points in time, and a linear or curved representation of the change in the voltage output 1836 can be used to arrive at an oxidation-reduction potential reading. If equilibrium has been reached, the determined oxidation-reduction potential value is presented to a user of the readout device 108 (step 1936). For example, the determined oxidation-reduction potential value can be presented as a measured voltage. If equilibrium has not been reached, the process can return to step 1920. After the ORP value has been output, the process can end.

Figure 20A:
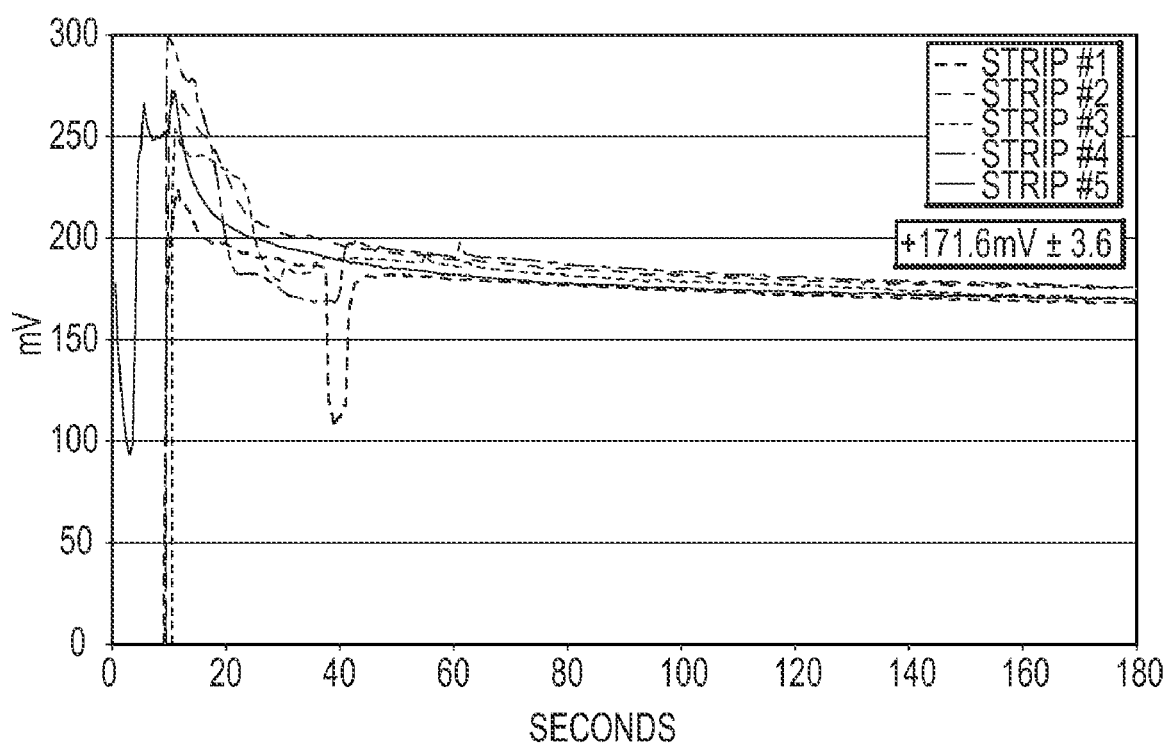
FIGS. 20A-B are graphs depicting exemplary ORP values for normal and trauma plasma using a test strip and readout apparatus in accordance with embodiments of the present invention.
Figure 20B:
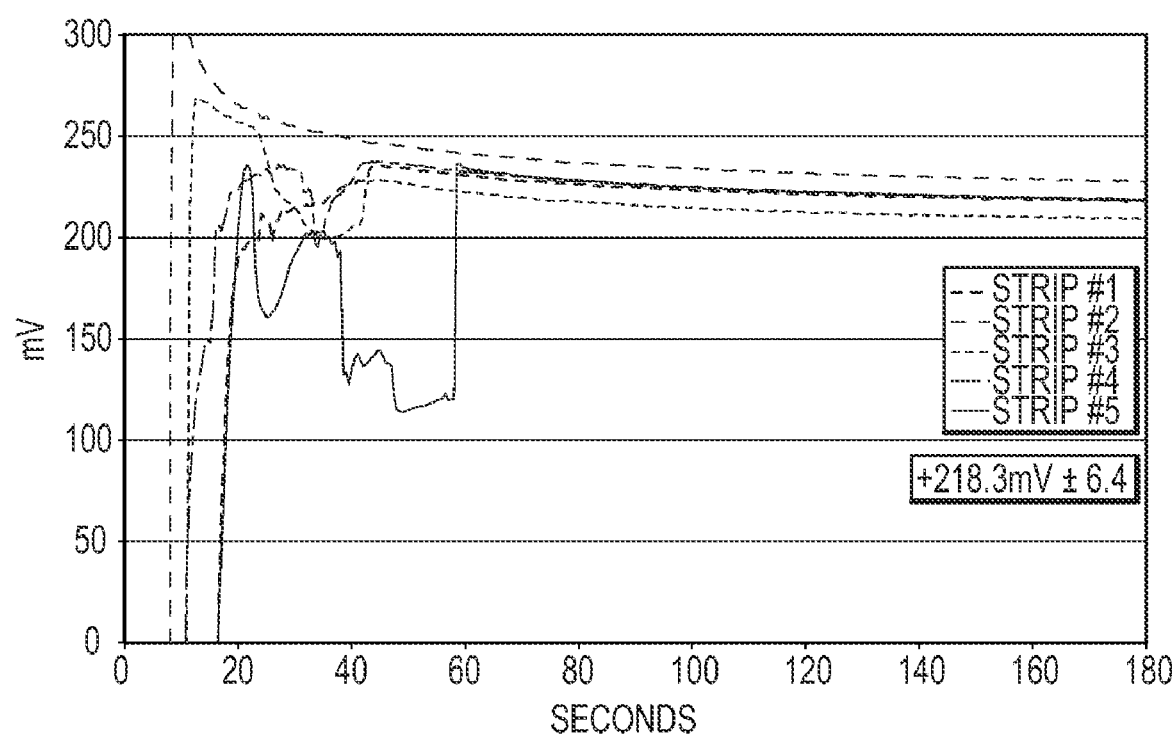

FIG. 20A is a graph depicting exemplary ORP values for normal plasma as read using a number of sample test strips in accordance with embodiments of the present invention. FIG. 20B is a graph depicting exemplary ORP values for trauma plasma using a number of different sample test strips. The test strip 104 used to obtain the ORP values is configured like the exemplary test strip 104 illustrated in FIG. 17. In addition, each test strip 104 incorporated a 104, 4% Agarose/3M KCl gel 708, a small salt bridge 232, a center spot comprising the reference cell 224, and sputtered platinum electrically conductive leads 204. The ORP values were read using readout electronics 1302 comprising a galvanostat, as generally shown in FIG. 18. The readout current applied by the readout electronics 1302 was $1 \times 10^{-9}$ amps. As shown in the figures, the potential (the vertical axis in the graphs) diminishes over time (the horizontal axis). In addition, a comparison of FIGS. 20A and 20B reveals that the ORP value, as expressed by the measured potential in millivolts, is higher for the trauma plasma (i.e., the plasma taken from an animal who has suffered a trauma) as compared to the measured ORP value for plasma from a normal patient. More particularly, after three minutes, the measured ORP of the trauma plasma was an average of 218.3 mV±6.4, while the average ORP for the normal plasma was 171.6 mV±3.6. In accordance with embodiments of the present invention, the ORP value used for diagnostic purposes would be the value arrived at after sufficient time has elapsed for the ORP to have settled such that the rate of change in measured ORP values is less than some selected amount. Alternatively or in addition, a curve fitting procedure can be used to extrapolate to an ORP value reported to the clinician or other user as a measured or derived ORP value.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. An oxidation-reduction potential test strip device, comprising:
   a substrate;
   a spacer layer interconnected to at least a portion of the substrate, wherein the spacer layer defines a sample chamber;
   a test strip overlay, wherein the test strip overlay is interconnected to at least a portion of the spacer layer;
   a first test lead supported by the substrate, the first test lead including:
      a first area within the sample chamber;
      a second area within a readout region;
   a second test lead supported by the substrate, the second test lead including:
      a first area within the sample chamber;
      a second area within the readout region;
   a reference cell, wherein the first test lead mirrors the second test lead;
   a reference lead, including;
      a first area in electrical contact with the reference cell;
      a second area within the readout region, wherein the first test lead, the second test lead, and the reference lead are accessible to a test device in the readout region when the test strip overlay is interconnected to the substrate, and wherein the first test lead, the second test lead, and the reference lead are on a common plane;

a filter, wherein at least a portion of the filter overlaps at least a portion of each of the first area of the first test lead, the first area of the second test lead, and the first area of the reference lead, and wherein the filter forms a bridge; and an electrolytic gel, wherein the electrolytic gel is in contact with the reference cell, and wherein at least a portion of the first test lead, at least a portion of the second test lead, the reference cell, the electrolytic gel, at least a portion of the reference lead, and the bridge are between the substrate and the test strip overlay when the test strip overlay is interconnected to the substrate.

2. An oxidation-reduction potential test strip device, comprising:

a substrate;

a spacer layer interconnected to at least a portion of the substrate, wherein the spacer layer defines a sample chamber;

a test strip overlay, wherein the test strip overlay is interconnected to at least a portion of the spacer layer;

a first test lead supported by the substrate, the first test lead including:
a first area extending into the sample chamber;
a second area extending from the sample chamber to a readout region;

a second test lead supported by the substrate, the second test lead including:
a first area extending into the sample chamber;
a second area extending from the sample chamber to the readout region;

a reference cell;

a reference lead, including:
a first area in electrical contact with the reference cell;
a second area extending from the reference cell to the readout region;

a filter, wherein at least a portion of the filter overlaps at least a portion of each of the first area of the first test lead, the first area of the second test lead, and the first area of the reference lead.

3. The device of claim 2, wherein at least a portion of the first test lead, the reference cell, at least a portion of the reference lead, and at least a portion of the filter are between the substrate and the overlay when the overlay is interconnected to the substrate.

4. The device of claim 3, wherein the overlay includes an aperture, and wherein the aperture corresponds to at least a portion of the sample chamber when the overlay is interconnected to the substrate.

5. The device of claim 4, wherein the filter is at least partially contained within the sample chamber.

6. The device of claim 2, further comprising:
a gel contained within a gel volume, wherein the gel comprises an electrolytic gel contained within the gel volume, and wherein the electrolytic gel is in contact with the reference cell.

7. The device of claim 6, wherein the gel volume is in communication with the sample chamber.

8. The device of claim 7, wherein the electrolytic gel comprises an Agarose and 3M KCl gel.

9. The device of claim 7, wherein the electrolytic gel comprises a hydroxyethyl cellulose gel.

10. The device of claim 2, wherein the reference cell includes a silver/silver chloride reference cell.

11. The device of claim 2, further comprising:
a fluid sample, wherein the fluid sample comprises a wetting agent that wets the filter that electrically interconnects the first area of the first test lead, the first area of the second test lead, and the first area of the reference lead.

12. The device of claim 11, wherein the fluid sample is whole blood.

13. The device of claim 2, wherein the first test lead, the second test lead, and the reference lead are formed from an electrically conductive material having a constant composition.

14. The device of claim 13, wherein the electrically conductive material having a constant composition is platinum.

15. The device of claim 2, wherein the first test lead, the second test lead, and the reference lead are accessible to a test device in the readout region when the overlay is interconnected to the substrate.

16. The device of claim 2, wherein the first test lead mirrors the second test lead.

17. The device of claim 16, wherein the first test lead, the second test lead, and the reference lead are located on a common plane.

18. A test strip, comprising:
a substrate, wherein a first surface of the substrate defines a first plane;
an overlay, wherein a sample chamber aperture that at least partially defines a sample chamber is formed in the overlay, wherein a first surface of the overlay defines a second plane, and wherein the first and second planes are parallel to one another;
a working electrode, including a sample chamber portion, and a readout portion, wherein the working electrode is located between the first plane defined by the first surface of the substrate and the second plane defined by the first surface of the overlay;
a counter electrode;
a reference cell, wherein the reference cell contains a material having a known electrical potential;
a bridge component, wherein the bridge component is in communication with the sample chamber and is electrically interconnected to the reference cell;
a reference lead, including a first portion that is in electrical contact with the reference cell and a readout portion;
a blood product, wherein the reference cell is electrically interconnected to the first test lead when the blood product is placed in the sample chamber, wherein the working electrode and the counter electrode comprise a material with a constant composition, and wherein the working electrode and the counter electrode mirror one another.

* * * * *